US006699176B1

(12) United States Patent
Khouri

(10) Patent No.: US 6,699,176 B1
(45) Date of Patent: Mar. 2, 2004

(54) EXTERNAL TISSUE DISTRACTION WITH EXPANDING FRAMES

(75) Inventor: Roger K. Khouri, Key Biscayne, FL (US)

(73) Assignee: Brava, LLC, Coconut Grove, FL (US)

(*) Notice: Subject to any disclaimer, the term of this patent is extended or adjusted under 35 U.S.C. 154(b) by 0 days.

(21) Appl. No.: 09/673,220

(22) PCT Filed: Dec. 1, 1999

(86) PCT No.: PCT/US99/28484

§ 371 (c)(1),
(2), (4) Date: Jul. 16, 2001

(87) PCT Pub. No.: WO00/32084

PCT Pub. Date: Jun. 8, 2000

Related U.S. Application Data

(63) Continuation-in-part of application No. 09/203,832, filed on Dec. 1, 1998, now Pat. No. 6,478,656.

(51) Int. Cl.⁷ .................................................. A61F 5/00
(52) U.S. Cl. ........................................................ 600/38
(58) Field of Search ............................. 450/1, 40, 39, 450/41–44, 65–70, 74–81; 600/38; 128/897–898

(56) References Cited

U.S. PATENT DOCUMENTS

| 532,236 A | 1/1895 | Hardesty |
| 936,434 A | 10/1909 | Eganhouse |
| 1,021,688 A | 3/1912 | Jeune |
| 1,312,619 A | 8/1919 | D'Orsay |
| 1,472,234 A | 10/1923 | Thomas |
| 2,012,755 A | 7/1935 | Demuth |
| 2,616,417 A | 11/1952 | Holbrook |
| 2,817,333 A | 12/1957 | Cole |

(List continued on next page.)

FOREIGN PATENT DOCUMENTS

| DE | 3019589 A1 | 8/1982 |
| EP | WO91/17727 | 11/1991 |
| UA | 1319853 | 6/1987 |
| WO | WO93/09727 | 5/1993 |

OTHER PUBLICATIONS

Francis, A.J. and Marks, R. Skin Stretching and Epidermopoiesis, Br. J. exp. Path. 58:35, 1977.

Squier, C.A. The Stretching of Mouse Skin in Vivo: Effects on Epidermal Proliferation and Thickness. The Journal of Investigative Dermatology 74:68, 1980.

Austad, E.D., Thomas, S.B., and Pasyk, K. Tissue Expansion: Dividend or Loan? Plastic and Reconstructive Surgery 78:63, 1986.

Pasyk, K.A., Argenta, L.C., and Austad, E.D. Histopathology of Human Expanded Tissue. Clinics in Plastic Surgery 14:435, 1987.

Olenius, M., Dalsgaard, C.J. and Wickman, M. Mitotic Activity in Expanded Human Skin. Plastic and Reconstructive Surgery 91:213, 1993.

De Witt, M.T., Handley, C.J. Oakes, B.W., and Lowther D.A. In Vitro Response of Chondrocytes to Mechanical Loading. The Effect of Short Term Mechanical Tension. Connective Tissue Research 12:97, 1984.

(List continued on next page.)

*Primary Examiner*—Samuel G. Gilbert
(74) *Attorney, Agent, or Firm*—Thompson Coburn, LLP

(57) ABSTRACT

A soft tissue expander comprises a frame comprised of inflatable members having in several embodiments a peripheral restrictor to force the frame to expand in only two dimensions. Various embodiments include frames arranged to be comprised of different polygonal shapes, frame members having internal mechanical restrictors, frames comprised of fusiform or cellular construction, and frames contained within two membranes that may also be filled with fluid.

36 Claims, 11 Drawing Sheets

U.S. PATENT DOCUMENTS

| | | | |
|---|---|---|---|
| 3,174,851 A | 3/1965 | Buehler et al. | |
| 3,382,867 A | 5/1968 | Reaves | |
| 3,568,675 A | 3/1971 | Harvey | |
| 3,631,853 A | 1/1972 | Burdette, Jr. | |
| 3,785,369 A | 1/1974 | Tallent | |
| 3,859,989 A | 1/1975 | Spielberg | |
| 3,874,387 A | 4/1975 | Barbieri | |
| 3,908,662 A | 9/1975 | Razhulov et al. | |
| 3,939,827 A | 2/1976 | Brunstetter | |
| 4,029,088 A | 6/1977 | Wu | |
| 4,175,554 A | 11/1979 | Gerow | |
| 4,368,883 A | 1/1983 | Tiktin | |
| 4,633,865 A | 1/1987 | Hengstberger et al. | |
| 4,653,484 A | 3/1987 | Cannon | |
| 4,665,903 A * | 5/1987 | Whitehead | 600/40 |
| 4,706,661 A | 11/1987 | Barrett | |
| 4,718,411 A | 1/1988 | Stewart | |
| 4,770,176 A | 9/1988 | McGreevy et al. | |
| 4,774,091 A | 9/1988 | Yamahira et al. | |
| 4,834,110 A | 5/1989 | Richard | |
| 4,856,498 A | 8/1989 | Osbon | |
| 4,856,499 A | 8/1989 | Kelly | |
| 4,930,674 A | 6/1990 | Barak | |
| 4,995,381 A | 2/1991 | Marmar et al. | |
| 5,059,211 A | 10/1991 | Stack et al. | |
| 5,141,516 A | 8/1992 | Detweiler | |
| 5,197,978 A | 3/1993 | Hess | |
| 5,234,401 A | 8/1993 | Yamanaka | |
| 5,254,113 A | 10/1993 | Wilk | |
| 5,273,900 A | 12/1993 | Boyce | |
| 5,274,074 A | 12/1993 | Tang et al. | |
| 5,276,015 A | 1/1994 | Khouri et al. | |
| 5,292,802 A | 3/1994 | Rhee et al. | |
| 5,308,889 A | 5/1994 | Rhee et al. | |
| 5,312,333 A | 5/1994 | Churinetz et al. | |
| 5,336,158 A | 8/1994 | Huggins et al. | |
| 5,344,396 A | 9/1994 | Clark, Jr. | |
| 5,370,685 A | 12/1994 | Stevens | |
| 5,464,450 A | 11/1995 | Busscemi et al. | |
| 5,468,220 A | 11/1995 | Sucher | |
| 5,476,091 A | 12/1995 | Johnson | |
| 5,476,478 A | 12/1995 | Jackson | |
| 5,536,233 A | 7/1996 | Khouri | |
| 5,571,074 A * | 11/1996 | Buckman et al. | 601/6 |
| 5,582,620 A * | 12/1996 | Hirsch | 606/192 |
| 5,636,643 A | 6/1997 | Argenta et al. | |
| 5,645,081 A | 7/1997 | Argenta et al. | |
| 5,653,744 A | 8/1997 | Khouri | |
| 5,662,583 A | 9/1997 | Khouri | |
| 5,669,870 A * | 9/1997 | Elist | 600/40 |
| 5,676,634 A | 10/1997 | Khouri | |
| 5,695,445 A | 12/1997 | Khouri | |
| 5,701,917 A | 12/1997 | Khouri | |
| 5,723,115 A | 3/1998 | Serrero | |
| 6,042,537 A | 3/2000 | Kaiser | |
| 6,083,912 A | 7/2000 | Khouri | |
| 6,086,866 A | 7/2000 | Kouri | |

OTHER PUBLICATIONS

Carter, D.R., Fyhrie, D.P. and Whalen, R.T. Trabecular Bone Density and Loading History: Regulation of Connective Tissue Biology by Mechanical Energy. J. Biomechanics 20:785, 1987.

Carter, D.R. Mechanical Loading History and Skeletal Biology. J. Biomechanics 20:1095, 1987.

Skoulis, T.G., Lovice, D., von Fricken, K., and Terzis, J.K. Nerve Expansion The Optimal Answer for the Short Nerve Gap. Behavioral Analysis. Clinical Orthopaedics and Related Research 314:84, 1995.

Wood, R.J., Adson, M.H., VanBeek, A.L., Peltier, G.L., Zubkoff, M.M., and Bubrick, M.P., Controlled Expansion of Peripheral Nerves: Comparison of Nerve Grafting and Nerve Expansion/Repair for Canine Sciatic Nerve Defects. The Journal of Trauma 31:686, 1991.

Manders, E.K., Saggers, G.C., Diaz–Alonzo, P. Finn, L., Sipio, J.C. Glumac, T., Au, V.K. Wong, R.K.M., and Mottaleb, M. Elongation of Peripheral Nerve and Viscera Containing Smooth Muscle. Clin. Plast. Surg. 14:551, 1987.

Stark, G.B., Hong, C., and Futrell, J.W. Rapid Elongation of Arteries and Veins in Rats with a Tissue Expander. Plastic and Reconstructive Surgery 80:570, 1987.

Wilson, E., Mai, Q., Sudhir, K., Weiss, R.H. and Ives, H.E. Mechanical Strain Induces Growth of Vascular Smooth Muscle Cells via Autocrine Action of PDGF. Journal of Cell Biology 123:741, 1993.

Sumpio, B.E., Banes, A.J., Link, W.G., and Johnson, G., Jr. Enhanced Collagen Production by Smooth Muscle Cells During Repetitive Mechanical Stretching. Arch. Surg. 123:1233, 1988.

Vandenburgh, H. and Kaufman, S. In vitro Model for Stretch–Induced Hypertrophy of Skeletal Muscle. Science 203:265, 1979.

Kim, K.H., Hong, C., and Futrell, J.W. Histomorphologic Changes in Expanded Skeletal Muscle in Rats. Plastic and Reconstructive Surgery 92:710, 1993.

Vandenburgh, H.H. Motion into mass: how does tension stimulate muscle growth? Medicine and Science in Sports and Exercise 19:S142, 1987.

Alway, S.E., Winchester, P.K., Davis, M.E., and Gonyea, W. Regionalized adaptations and muscle fiber proliferation in stretch–induced enlargement. Journal of Applied Physiology 66:771, 1989.

Finn, L.S., Saggers, G., Manders, E.K., and Rose, R.C. Soft Tissue Expansion to Elongate the Small Bowel. Surgical Forum 39:604, 1988.

Narayan, D., Castro, A., Jackson, I.T., and Herschman, B. Tissue expanders in the gut: a histological and angiographic study. J.R. Coll. Surg. Edinb. 37:402, 1992.

Bianchi, A. Intestinal Loop Lengthening A Technique for Increasing Small Intestinal Length. Journal of Pediatric Surgery 15:145, 1980.

Kimura, K. and Soper, R.T. A New Bowel Elongation Technique for the Short–Bowel Syndrome Using the Isolated Bowel Segment Lowa Models. Journal of Pediatric Surgery 28:792, 1993.

Rannels, D.E. Role of physical forces in compensatory growth of the lung. American Journal of Physiology 257:L179, 1989.

Russo, L.A., Rannels, S.R., Laslow, K.S., and Rannels, D.E. Stretch–related changes in lung cAMP after partial pneumonectomy. American Journal of Physiology: Endocrinology and Metabolism 20:E261, 1989.

Curtis, A.S.G. and Seehar, G.M. The control of cell division by tension or diffusion. Nature 274:52, 1978.

Brunette, D.M. Mechanical Stretching Increases the Number of Epithelial Cells Synthesizing DNA in Culture. J. Cell. Sci. 69:35, 1984.

Jain, M.K., Berg, R.A., and Tandon, G.P. Mechanical stress and cellular metabolism in living soft tissue composites. Biomaterials 11:465, 1990.

Rodriguez, E.K., Hoger, A., and McCulloch, A.D. Stress Dependent Finite Growth in Soft Elastic Tissues. J. Biomechanics 27:455, 1994.

Folkman, J. and Moscona, A. Role of cell shape in growth control. Nature 273:345, 1978.

Urschel, J.D., Scott, P.G. and Williams, H.T.G. The effect of mechanical stress on soft and hard tissue repair; a review. British Journal of Plastic Surgery 41:182, 1988.

Ryan, T.J. Biochemical consequences of mechanical forces generated by distention and distortion. J. Am. Acad. Dermatol 21:115, 1989.

Watson, P.A. Function follows form: generation of intracellular signals by cell deformation. FASEB J. 5:2013, 1991.

Vandenburgh, H.H. Mechanical forces and their second messengers in stimulating cell growth in vitro. American Journal of Physiology 262:R350, 1992.

Takei, T., Mills, I., Katsuyuki, A., and Sumpio, B.E. Molecular Basis for Tissue Expansion: Clinical Implications for the Surgeon. Plastic and Reconstructive Surgery 101:247, 1998.

Ruoslahti, E. Stretching Is Good for a Cell. Science 276:1345, 1997.

Neumann, C.G. The Expansion of an Area of Skin by Progressive Distention of a Subcutaneous Balloon. Plastic and Reconstructive Surgery 19:124, 1957.

Radovan, C. Tissue Expansion in Soft Tissue Reconstruction. Plastic and Reconstructive Surgery 74:482, 1984.

Mackinnon, S.E. and Gruss, J.S. Soft tissue expanders in upper limb surgery. The Journal of Hand Surgery. 10A:749, 1985. Argenta; L.C. Controlled tissue expansion in reconstructive surgery. British Journal of Plastic Surgery 37:520, 1984.

Manders, E.K., Schenden, M.J., Furrey, J.A., Hetzler, P.T., Davis, T.S. and Graham, W.P. Soft–Tissue Expansion: Concepts and Complications. Plastic and Reconstructive Surgery 74:493, 1984.

Mustoe, T.A., Bartell, T.H. and Garner, W.L. Physical, Biomechanical, Histologic, and Biochemical Effects of Rapid versus Conventional Tissue Expansion. Plastic and Reconstructive Surgery 83:687, 1989.

Marcus, J., Horan, D.B., and Robinson, J.K. Tissue expansion: past, present, and future. The Journal of the American Academy of Dermatology 23:813, 1990.

Johnson, T.M., Lowe, L., Brown, M.D., Sullivan, M.J., and Nelson, B.R. Histology and Physiology of Tissue Expansion. J. Dermatol Surg. Oncol. 19:1074, 1993.

Bennett, R.G. and Hirt, M. A History of Tissue Expansion: Concepts, Controversies, and Complications. J. Dermatol Surg. Oncol. 19:1066, 1993.

Becker, H. Breast Reconstruction Using an Inflatable Breast Implant with Detachable Reservoir. Plastic and. Reconstructive Surgery 73:678, 1984.

Chisolm, E.M., Marr, S., Macfie, J., Broughton, A.C. and Brennan, T.G. Post–mastectomy breast reconstruction using the inflatable tissue expander. Br. J. Surg. 73:817, 1986.

Slavin, S.A. and Colen, S.R. Sixty Consecutive Breast Reconstructions with the Inflatable Expander: A Critical Appraisal. Plastic and Reconstructive Surgery. 86:910, 1990.

McGeorge, D.D. The "Niplette": an instrument for the non–surgical correction of inverted nipples, British Journal of Plastic Surgery 47:46, 1994.

Herzenberg, J.E., Davis, J.R., Paley, D., and Bhave, A. Mechanical Distraction for Treatment of Severe Knee Flexion Contractures. Clinical Orthopaedics and Related Research 301:80, 1994.

Volkov, M.V. and Oganesian, O.V. Restoration of Function in the Knee and Elbow with a Hinge–Distractor Apparatus. The Journal of Bone and Joint Surgery 57A:591, 1975.

Mingli, Z., Dawei, W., and Lan, H. The Application of Skin External Expander to Postburn Advanced Scar Contracture. Plastic and Reconstructive Surgery 96:1600, 1995.

Cohen, B.H. and Cosmetto, A.J. The Suture Tension Adjustment Reel. J. Dermatol. Surg. Oncol. 18:112, 1992.

Ilizarov, G.A. The Tension–Stress Effect on the Genesis and Growth of Tissues: Part I The Influence of Stability of Fixation and Soft–Tissue Preservation. Clinical Orthopaedics and Related Research 238:249, 1989.

Ilizarov, G.A. The Tension–Stress Effect on the Genesis and Growth of Tissues: Part II The Influence of the Rate and Frequency of Distraction. Clinical Orthopaedics and Related Research 239:263, 1989.

Ilizarov, G.A. Clinical Application of the Tension–Stress Effect for Limb Lengthening. Clinical Orthopaedics and Related Research 250:8, 1990.

Coleman, S.S. and Scott, S.M. The Present Attitude Toward the Biology and Technology of Limb Lengthening. Clinical Orthopaedics and Related Research 264:76, 1991.

Paley, D., Rumley, T.O., and Kovelman, H. The Ilizarov Technique: A Method to Regenerate Bone and Soft Tissue. Advanced Plast Reconstr Surg 7:1, 1991.

Villa, A., Paley, D., Catagni, M.A., Bell, D., and Cattaneo, R. Lengthening of the Forearm by the Ilizarov Technique. Clinical Orthopaedics and Related Research 250:125, 1990.

Stricker, S.J. Ilizarov Lengthening of a Posttraumatic Below Elbow Amputation Stump. Clinical Orthopaedics and Related Research 306:124, 1994.

McCarthy, J.G., Schreiber, J., Karp, N., Thorne, C.H., and Grayson, B.H. Lengthening the Human Mandible by Gradual Distraction. Plastic and Reconstructive Surgery 89:1, 1992.

Polley, J.W. and Figueroa, A.A. Management of Severe Maxillary Deficiency in Childhood and Adolescence Through Distraction Osteogenesis With an External, Adjustable, Rigid Distraction Device. The Journal of Cranofacial Surgery 8:181, 1997.

Cohen, S.R., Burstein, F.D., Stewart, M.B., and Rathburn, M.A. Maxillary–Midface Distraction in Children with Cleft Lip and Palate: A Preliminary Report. Plastic and Reconstructive Surgery 99:1421, 1997.

Cohen, S.R., Rutrick, R.E., and Burstein, F.D. Distraction Osteogenesis of the Human Craniofacial Skeleton: Initial Experience with a New Distraction System. The Journal of Cranofacial Surgery 6:368, 1995.

Block, M.S., Cervini, D., Chang, A. and Gottsegen, G.B. Anterior Maxillary Advancement Using Tooth–Supported Distraction Osteogenesis. J. Oral Maxillofac. Surg. 53:561, 1995.

Sugihara, T., Kawashima, K., Igawa, H., Ohura, T., Yamamura, M., and Ohata, N. Mandibular lengthening by gradual distraction in humans. European Journal of Plastic Surgery 18:7, 1995.

Rachmiel, A., Potparic, Z., Jackson, I.T. et al. Midface advancement by gradual distraction. British Journal of Plastic Surgery 46:201, 1993.

Copy of *Enlargement Book*, ©1990 Topco Books.

Copy of *An Anthology Of Plastic Surgery*, edited by Harry Hayes, Jr., M.D., specifically Section 6 entitled "Quackery and Nostrums", Aspen Publishers, Inc., 1986, pp. 163–175.

Article entitled "The Tension–Stress Effect on the Genesis and Growth of Tissues—Part I. The Influence of Stability of Fixation and Soft–Tissue Preservation" by Gavriil A. Ilizarov, AM., M.D., Ph.D., from *Clinical Orthopaedics and Related Research*, from Section III, entitled "Basic Science And Pathology", No. 238, Jan. 1989, pp. 249–281.

Article entitled "The 'Niplette': an instrument for the non-surgical correction of inverted nipples" by D.D. McGeorge, from *British Journal Of Plastic Surgery* 1994, pp. 46–49.

Copy of *How To Enlarge Your Penis*, ©1988 House One, expurgated version.

Brochure entitled "Nipple Enlargement System" by Joel Kaplan, Ph.D., 1993.

Article entitled "The Ilizarov Technique: A Method To Regenerate Bone And Soft Tissue" by Dror Paley, M.D., et al., pp. 1–41.

Article entitled "The Callotasis Method of Limb Lengthening" by Roberto Aldegheri, M.D., et al., from *Clinical Orthopaedics and Related Research*, No. 241, Apr. 1989, pp. 137–145.

Article entitled "Histophathology of Human Expanded Tissue" by Krystyna A. Pasyk, M.D. et al., from *Clinics in Plastic Surgery*, vol. 14, No. 3, Jul. 1987, pp. 435–445.

Article entitled "The Expansion of an Area of Skin by Progressive Distention of a Subcutaneous Balloon—Use of the Method for Securing Skin for Subtotal Reconstruction of the Ear", by Charles G. Neumann, M.D. from *Plastic And Reconstructive Surgery*, Feb. 1957, pp. 124–130.

Article entitled "Tissue Expansion in Soft–Tissue Reconstruction" by Chedomir Radovan, M.D., from *Plastic and Reconstructive Surgery*, Oct. 1984, pp. 482–492.

Article entitled "Elongation of Peripheral Nerve and Viscera Containing Smooth Muscle" by Ernest K. Manders, M.D., et al., from *Clinics in Plastic Surgery*, vol. 14, No. 3, Jul. 1987, pp. 551–562.

*Microvascular Anastomoses Utilizing New Intravascular Stents* by Moskovitz et al., Ann Plat Surg, vol. 32, pp. 612–618, 1994.

*Sutureless Vasovasostomy: New Technique Using Experimental Microclip in Rat Model* by Askill et al., Urology, vol. 40, No. 2, 191–4, 1992.

*A New Method for Microvascular Anastomosis: Report of Experimental and Clinical Research* by Kirsch et al., The American Surgeon, vol. 12, No. 58, pp. 722–727, 1992.

*Experimental Study of Microvascular Anastomosis Using a Dissolvable Stent Support in the Lumen* by Cong et al., Microsurgery, vol. 12, p. 67–71, 1991.

*Microvascular Anastomosis Using Polyethylene Glycol 4000 and Fibrin Glue* by Kaiji et al., British Journal of Plastic Surgery, vol. 42, pp. 54–58, 1989.

*The Temporary Stent Technique: An Easier Method of Micro–Venous Anastomosis* by Wei et al., British Journal of Plastic Surgery, vol. 42, pp. 54–58, 1989.

Article entitled "Rapid Elongation of Arteries and Veins in Rats with a Tissue Expander" by G. Björn Stark, M.D., et al., from *Plastic And Reconstructive Surgery*, Oct. 1987, pp. 570–581.

Lorber, M. and Milobsky, S. Stretching of the Skin in vivo. A Method of Influencing Cell Division and Migration in the Rat Epidermis. The Journal of Investigative Dermatology 51:395, 1968.

Scheck, M. Translation of The Classic by Julius Wolff: Concerning the Interrelationship Between Form and Function of the Individual Parts of the Organism. Clinical Orthopaedics and Related Research 228:2, 1988.

Star, G.B., Dorer, A., Walgenbach, K.J., Grunwald, F., and Jaeger K. The creation of a small bowel pouch by tissue expansion—an experimental study in pigs. Langenbecks Archive for Chirurgie 375:145, 1990.

Versaci, A.D. Reconstruction of a Pendulous Breast Utilizing a Tissue Expander. Clinics in Plastic Surgery 14:499, 1987.

Didcott, C.C. and Schnaid, E. Treatment of flexion contractures of the knee joint with a slow continuous stretch apparatus. South African Journal of Surgery 26:173, 1988.

Hodgkinson, P.D. The Use of Skeltal Traction to Correct the Flexed Pip Joint In Dupuytren's Disease. Journal of Hand Surgery 19B:534, 1994.

Aldegheri, R., Renzi–Brivio, L., and Agostini, S. The Callotasis Method of Limb Lengthening. Clinical Orthopaedics and Related Research 241:137, 1989.

Rosen, H.M. Facial Skeletal Expansion: Treatment Strategies and Rationale. Plastic and Reconstructive Surgery 89:798, 1992.

Chamay, A. and Tschantz, P. Mechanical Influences In Bone Remodeling. Experimental Research On Wolff's Law Journal of Biomechanics 5:173, 1972.

Bolinder et. al, Study of Acute Effects of Insulin–like Growth Factor I and II in Human Fat Cells, Journal of Clinical Endocrinology and Metabolism, vol. 65, pp. 732–737, 1987.

Hayes, Jr., M.D., Harry *An Anthology Of Plastic Surgery*, specifically Section 6 entitled "Quackery and Nostrums", Aspen Publishers, Inc., 1986, pp. 163–175.

Schmitz, et al., In Vivo Metabolic Action Of Insulin–Like Growth Factor I in Adult Rats, Diabetologia, 34:144–149, 1991.

Smith et al., Insulin–Like Growth Factor–I Is an Essential Regulator of the Differentiation of 3T3–L1 Apidocytes, The Journal of Biological Chemistry, vol. 263, No. 19, pp. 9402–9408, Jul. 5, 1988.

\* cited by examiner

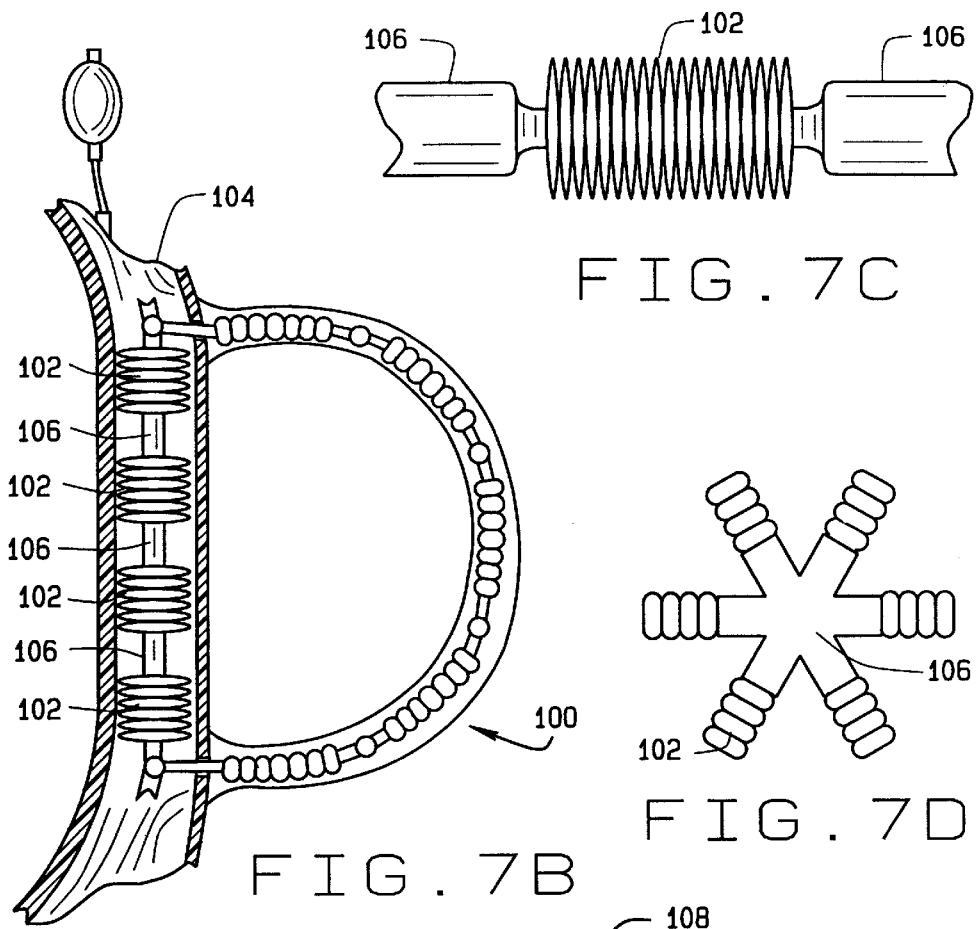
FIG. 7C
FIG. 7B
FIG. 7D
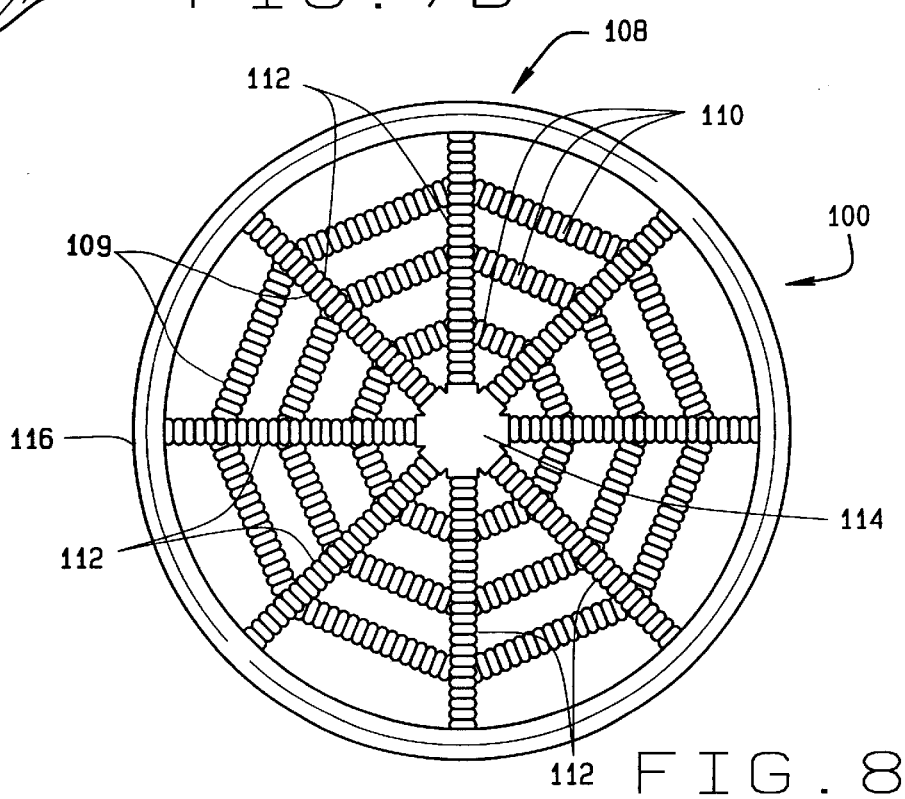
FIG. 8

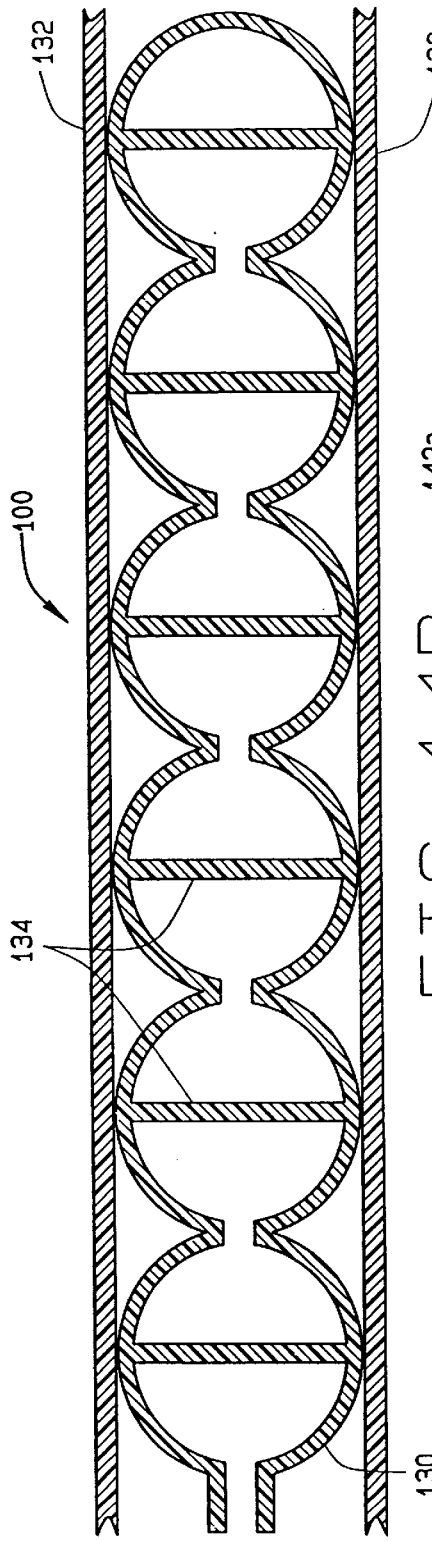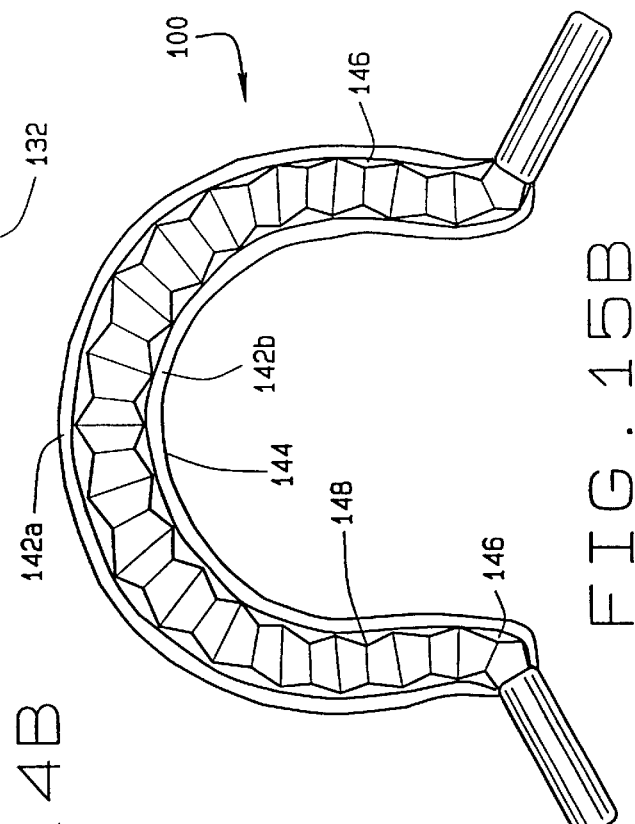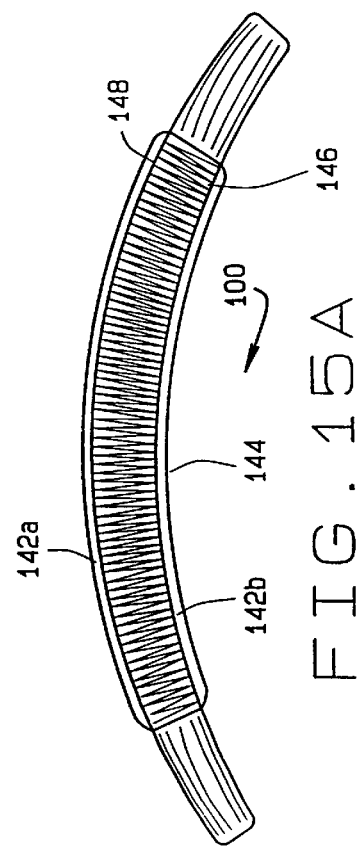
FIG. 14B
FIG. 15B
FIG. 15A

EXTERNAL TISSUE DISTRACTION WITH EXPANDING FRAMES

RELATED APPLICATION

This application is a continuation-in-part application of U.S. application Ser. No. 09/203,832 filed Dec. 1, 1998 now U.S. Pat. No. 6,478,656.

BACKGROUND AND SUMMARY OF THE INVENTION

It is well accepted by scientific authorities that living tissue can be made to grow in response to a gentle, sustained tensile force which, in the prior art, has generally been induced through a mechanical arrangement. This phenomenon has been demonstrated in many kinds of living tissues including skin, bone, muscle, nerves, blood vessels, lungs and even in isolated tissue cultures. (See references attached in Exhibit A.) The physiological mechanisms which contribute to this universal property of living tissue have recently been reviewed. (See references attached in Exhibit A.) Furthermore, many useful medical devices have been developed which rely on this universal property of tensile force induced tissue growth. (See references attached in Exhibit A.) However, as mentioned, these prior art devices typically operate through a mechanically induced tensile force occasioned by hooks, pins, or other more invasive, complication prone surgical procedures for establishing mechanical procedures for establishing mechanical connections between which the tensile forces are created.

The inventor herein has himself previously invented a non-invasive, mechanical device for applying a sustained tensile force to a soft tissue or skin surface to thereby enlarge a patient's soft tissue. The inventor has received patents on these various non-invasive devices and methods including U.S. Pat. Nos. 5,695,445 and 5,662,583, the disclosures of which are incorporated herein by reference. While the inventor's work is continuing, he has engaged in rigorous clinical testing as a necessary predicate to receiving FDA approval which has confirmed the clinical effectiveness of his devices and methods in enlarging soft tissue including female breasts. More particularly, the device used in his clinical studies utilizes a low level vacuum to apply a tensile force on the skin surface of a breast, with an adhesive surface being used to seal the vacuum against the patient's skin. This device takes the form of a bra-like appliance which is portable and aesthetically acceptable in that its presence is virtually undetectable as it is worn by the patient during her daily activities. These prototype devices being used are fully operational and have confirmed the effectiveness of a sustained tensile force in achieving soft tissue growth and enlargement.

As the inventor has continued his further work and development in this area, he has continued to seek ways to improve his devices with respect to their effectiveness, aesthetics, and comfort to a potential patient. One of the more difficult problems to solve with the inventor's vacuum based devices has been the need to maintain the vacuum as the device is worn throughout daily activities and yet be so unobtrusive as to be undetectable to those around the patient and who may be in close proximity to her. The inventor has developed one such device in which a vacuum may be established as the patient begins her day, and then supplemented or even reestablished with a hand operated pump and valve mechanism should the vacuum become reduced to an unacceptable level or otherwise escape as the patient twists and bends her torso in her normal daily activities.

However, even with this particular arrangement, the inventor has sought to further improve his device by developing an alternative means for delivering a distracting force and yet permitting the patient to twist and turn her torso as needed without the inconvenience of reestablishing or supplementing the vacuum needed to achieve the soft tissue enlargement. While the inventor had previously conceived of various mechanical arrangements for establishing and maintaining a tensile force in this application, and indeed received U.S. Pat. No. 5,662,583 issued Sep. 2, 1997 for several of them, these arrangements were subject to their own difficulties. For example, several of them required a somewhat elaborate arrangement of mechanical springs, wires, interleaved shell members, or other such mechanical and moving parts as to be fairly intricate and perhaps difficult to reliably implement. Another embodiment disclosed and claimed in the '583 patent included utilizing an intermediate material which could be caused to shrink upon curing. While such a curably shrinking material could effectively create the desired tensile force, it may possibly require replacement of the once shrunk intermediate material at least on a daily basis as the patient would remove the bra and then reapply it, depending upon the material chosen and its capability for cycling, on demand. For these reasons, among others, the inventor has previously focused his activities on vacuum based devices.

In order to solve the potential difficulties with maintaining a vacuum in the vacuum based devices and the intricacies of the mechanical devices, the inventor herein has previously succeeded in conceiving and developing a further mechanical embodiment for creating the required tensile force in a soft tissue expander. More particularly, the inventor has conceived of utilizing a "memory material" which may be moved into a first physical arrangement for being adhered to the surface of the soft tissue desired to be enlarged, and then causing the memory material to transform into its second physical arrangement to thereby create the required tensile force. The first physical arrangement may be a non-memory arrangement and the second physical arrangement may be the memory arrangement. More particularly, the memory material may comprise one of the shape memory alloys, an example of which is Nitinol as disclosed in U.S. Pat. No. 3,174,851, the disclosure of which is incorporated herein by reference. Nitinol and some other related nickel-titanium or copper-zinc-aluminum methyl alloys have a "shape memory affect" that has been previously utilized in a number of useful medical devices. These include as an orthodontic arch where the arch is cooled and then placed in the patient's mouth which warms it and moves it into a stressed shape to exert pressure on the patient's teeth. Still other medical applications known to the inventor are as an expandable filter which is used in the blood vessels and as a bony anchor. These shape memory alloys or "SMA" have two crystalline phase forms with a transition temperature that can be set at approximately normal body surface temperature (approximately 30 degrees centigrade). At temperatures greater than this transition temperature, these alloys prefer the Austenite phase while at lower temperatures they prefer the Martensite phase. The Martensite phase crystal structure consists of a series of planes that may be readily displaced allowing the alloy to be easily deformed in nearly any direction. When the alloys are heated to a temperature at or above the transition temperature, the Austenite crystal phase is preferred which forces the planes to revert back into their original configuration. In effect, this hardens the alloys and forces them to spring back and restore their original or "set" shape. These alloys may also be activated by passing an electrical current through them. Thus, these metal alloys give the appearance of "remembering" their originally set shape. Cooling and heating these alloys below and above the transition temperature can be repeated thousands of times, each time changing the property of the alloy from being soft for fashioning into a second physical arrangement to rigid which causes them to spring back into their set shape or original physical arrangement. The set shape or "shape memory" may be set by imprinting the desired form or shape into the alloy and then heating it to temperatures approximating 500 degrees centigrade.

In addition to shape memory alloys, certain plastics may also be engineered to move between a first physical arrangement and a second physical arrangement as a function of temperature, as known to those of ordinary skill in the art. These plastics may also be utilized as a "memory material" suitable for implementing the present invention.

In implementing these memory materials, the cups or domes described in one or more of the inventor's previous patents could include some form of memory material in their fabric. Below body temperature, these domes would be soft and conformable to the shape and contour of the underlying breast or soft tissue surface to be enlarged. As the patient's body temperature heats the domes and memory material, they will tend to revert and spring back to their previously imprinted "memory" of a deeper/wider dome. If appropriately adhered to the underlying soft tissue surface or skin, this reversion or "springing back" of the memory material will then impart a tensile force to the underlying skin or tissue surface as would be effective for creating soft tissue enlargement in a suitable therapeutic regimen. Additionally, a small battery operated electronic circuit may be provided to activate and increase the tension of some of the fibers that would be set for a higher transition temperature. This would allow the bra to operate in an intermittent duty cycle in addition to maintaining a constant tension.

In order to appropriately distribute the tensile force while at the same time adhering the memory material to the underlying tissue, a layer of gel, or an air or other fluid filled bladder, may be an appropriate interface between the skin and layer of memory material, and an appropriate adhesive substance placed between the layer of gel and the underlying skin. As the inventor has disclosed in one or more of his prior patents, this adhesion could be effected with any one of a well known group of surgical adhesives which are known to bond appropriately to a skin surface without damage for extended periods of time. This may preferably be a layer of sticky silicone gel. Alternatively, the inventor has further conceived of implementing the principles of surface tension as a non-abrasive way of achieving this necessary adhesion. More particularly, a fluid may be placed on the gel layer, or on the patient's soft tissue just prior to application of the bra, and the inventor has found that the forces attributable to surface tension are sufficient to maintain an appropriate adherence between the soft tissue and the gel as the memory material transitions physical arrangement to thereby impart the desired tensile force. Thus, the inventor has conceived of utilizing a memory material for mechanically inducing a tensile force in an appropriately chosen soft tissue site, as well as the concept of utilizing a thin layer of fluid as an interface for creating a surface tension to maintain adherence between a layer of gel or other intermediary layer to insure a distribution of the tensile force across the skin surface to thereby avoid undesired shear forces or other concentrating effects which might cause undesired abrasion or damage to the skin surface.

As a continuation of the inventor's efforts, he has conceived of a further embodiment for applying a distractive force to an underlying soft tissue. This newest embodiment incorporates many of the advantages of the inventor's prior embodiments while providing even greater control over the application of the force and dramatically improving its user friendliness including its physical size and contours. As can be appreciated, this aspect of the invention is important as its appearance as it is worn can be in an area of a person's physique ordinarily considered to be private, i.e. such as a bra over a woman's breasts.

In the inventor's newest embodiment, a thin expandable rubber-like membrane that can espouse the contours of the small relatively flat tissue at rest and can stretch and expand to the contour of the enlarged distracted tissue. (Breast in the most common application but face might be an emerging one) is provided as well as an expansion mechanism or frame that is mechanically linked to the membrane and can stretch it to form a dome-like structure. In one version of this newest embodiment, a membrane is provided both above and below the frame, and may encapsulate it.

These newest embodiments provide a quantum leap in the practicality of the external tissue enlargement device. By eliminating the vacuum components, some of the constraints of the bladder rim (forces, pressures and areas in some combination and fashion still need to be equilibrated), and the need for multiple cup sizes, patient compliance, public acceptance and cost will be greatly improved. For the breast enlargement application, this new embodiment will be as simple to use and not bulkier than a padded bra.

Another related application of tension induced soft tissue generation is the rejuvenation of the aged face. Modern plastic surgery has realized that in facial rejuvenation, a face fill is just as important as a face lift. In other words, plumping up the face and restoring the subcutaneous fat atrophy associated with aging is nearly as effective as a face lift. Cosmetic surgeons currently fill up the wrinkle lines with fat grafts or collagen injections and significantly improve the facial stigma of old age. A wrinkle patch that induces tissue growth under the wrinkles or a rejuvenating face mask that fills up the lost fat are potentially very useful applications of this technology of tension induced tissue growth.

This newest embodiment aims to further refine the design of the mechanical expansion frames found in the inventor's prior patents and to disclose the use of positive fluid pressure (gas or liquid) as the transducing force that can be used to expand these frames and create the necessary distractive force. As these tissue expansion frames expand, they are capable of rising from relatively flat surfaces to progressively deeper dome-like shells. When these novel types of frames are mechanically connected to the surface of the tissues (either through adhesives, through surface tension effect, or otherwise), their expansion pulls up the tissues, inducing a distractive force which causes them to grow.

Fluid pressure, however, is isotropic and will cause a simple inflatable structure to expand in all three dimensions, opening up like a balloon. The desired effect, on the other hand, is that of inducing a flat frame to rise as a three-dimensional dome-like shell. In other words the leaflets of the frame should not open up; rather, the desired expansion should induce the frame to keep a relatively even thickness forcing it to spread out only in two dimensions. By circumferentially constraining the frame either at its edges or though its inherent tailored design, the induced surface spread should cause it to rise as a dome-like shell. The three-dimensional surface contour of the dome, its excursion, and the force of deformation depend upon the fluid pressure applied and the mechanical design of the inflatable structure. Under the effect of positive fluid pressure, the rising and progressively deeper dome-like shell pulls up and distracts the tissues that are mechanically connected to its concave surface, inducing them to grow.

The main subject of this newest embodiment is the concept of a frame, which, in its resting state, can espouse the surface contour of the body part to be enlarged. This frame is connected to the underlying tissues either through a glue or layer of adhesive or through surface tension effect. A compliant expandable membrane may be additionally used to serve as the interface and the mechanical link between the frame and the surface of the tissue to be distracted. Although, other means for securing the underlying soft tissue to the frame may be used. For example, surgical attachment may be used. The frame is designed such that it can be inflated and under the effect of internally applied positive fluid pressure it can rise into progressively deeper domes. The range of excursion could stretch from flat to a nearly spherical surface in order to maximize the amount of induced distractive force. Furthermore, the surface contour of the expanded frame may be designed such that it can deviate from the perfect sphere as it expands into a dome. This is needed to evenly expand a complex surface, or to differentially expand certain areas relative to others. (i.e. from flat to tear drop in the case of a breast or more complex surface contour in the case of a full face). The force and extent of elevation of this frame can be gauged by the amount of fluid pressure applied. This frame will need to distribute the counterforce of distraction through its rim pressing against the tissues at the periphery. Therefore, as in the previous inventions, there is a need to equilibrate the pressures, forces, and/or the surface areas of the frame in relation to the contact surface area of the non-expanding surrounding rim.

Fluids under positive pressure have many useful applications. The inventor is, however, interested in those that result in rigid dome-like shell structures as compared to the simple inflatable balloon or ring-like tire. Applications more relevant to the present invention are the inflatable self supporting dome-like structures such as the ones used to cover stadiums or the umbrella-like and shield-like antennae deployed in aerospace applications.

While fluids under positive pressure are used in medicine to inflate tissue expanders (inflatable silicone shells), these devices are internal. They are surgically inserted under the skin and they stretch it from the inside out instead of the external device described herein which can raise the surface of the tissue by pulling it up from the outside. Furthermore these common tissue expander devices inflate like simple balloons instead of converting a flat frame into a dome-like shell.

In the present invention, the required effects of positive pressure inflation are mostly linear (one-dimensional), or preferably mostly sheet like (two-dimensional) expansion of the frame instead of the inherent three-dimensional ballooning effect of unrestrained inflation. To achieve this dimensional restriction, the basic building block may include one or more of the following several alternative design options.

In its simplest form, the expanding frame consists of an airtight flat bladder made out of an inner and an outer expandable membrane interconnected by a network of non-expandable links. The mechanical properties, the thickness, and the tailoring of these membranes are adjusted such that with inflation, this bladder which cannot blow up like a balloon, will distort into a dome-like shell (see FIG. 1 and its description below). This might be a mechanically inefficient means of using pressure to pull up the tissues, but it is contemplated by the inventor that it would be effective in this application. Other more efficient designs might be used, at least some of which are described below and others of which would be apparent to those of ordinary skill in the art having once gained the benefit of the inventor's disclosure herein.

The simplest building block for the mechanically more efficient design is the piston-in-cylinder or some sort of corrugated accordion bellows that can expand in only one dimension under the effect of applied fluid pressure. A two-dimensional expansion will result from linking these one-dimensional blocks at various angles. The simplest geometrical design could be considered to be that of repeating triangles. When each side of the triangle expands one-dimensionally, the result is a two dimensional stretch of the construct. If, in addition, the edges of the repeating triangular pattern are constrained and prevented from stretching, the frame is forced to rise as a dome. This is the structural basis for the geodesic dome design (see FIGS. 7*a*&*b* and the discussion below). A person of ordinary skill in the art of computer aided design knows that any complex three-dimensional surface can be reduced to a series of adjacent triangles. Expanding the sides of these judiciously designed array of triangles can induce a controlled and preferential distraction of any complex body surface that needs to be enlarged. Other geometric shapes and arrangements for the frame itself may be used, as is described in greater detail below. Additionally, the details of the structure used for the "legs" or struts which form the frame can be varied to provide other ways for restraining the frame movement as it is expanded in order to achieve the desired application of a distractive force.

While some of the principal advantages and features of the invention have been discussed above, a fuller understanding of the invention may be attained by referring to the drawings and description of the preferred embodiment which follow.

BRIEF DESCRIPTION OF THE DRAWINGS

FIGS. 7*a–d* depict a frame constructed in a geodesic configuration, and a detail view of a frame member.

FIG. 8 depicts a front view of a florentine dome frame construction.

FIGS. 15a&b are side views of a frame member which is sealed and filled with a fluid to enhance its inflatability.

DETAILED DESCRIPTION OF THE PREFERRED EMBODIMENT

Figure 1:
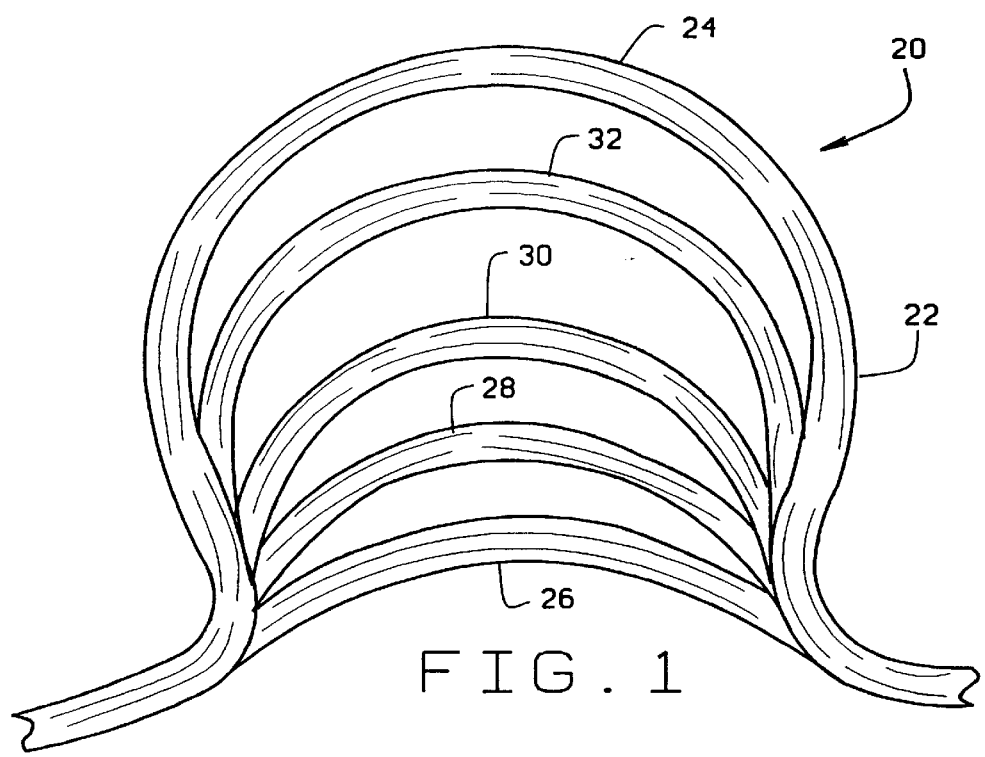
FIG. 1 depicts in cross section the successive positions of a memory material as it transitions from a first physical arrangement to a second physical arrangement.

As shown in FIG. 1, a dome 20 of memory material 22 may be treated to "set" its shape in a memory as depicted in position 24. As used in the invention first disclosed in the parent to the present patent, the memory material 20 may be chosen to be a shape memory alloy having a transition temperature at approximately body surface temperature which is approximately 30 degrees centigrade. As the shape memory alloy is taken to a lower temperature, it may then be fashioned into a shape such as that shown at position 26. Then, as the temperature of the memory material approaches its transition temperature, it may successively taken on the shape shown at positions 28, 30, 32, and then reaching its memory position at position 24. Thus, a memory material may be used in the parent invention to provide a bra or other dome like structure which may be fashioned into a relatively shallow shape but which upon reaching its transition temperature deflects to a significant degree in order to provide the mechanism for creating a mechanical tensile force in an underlying soft tissue.

Figure 2:
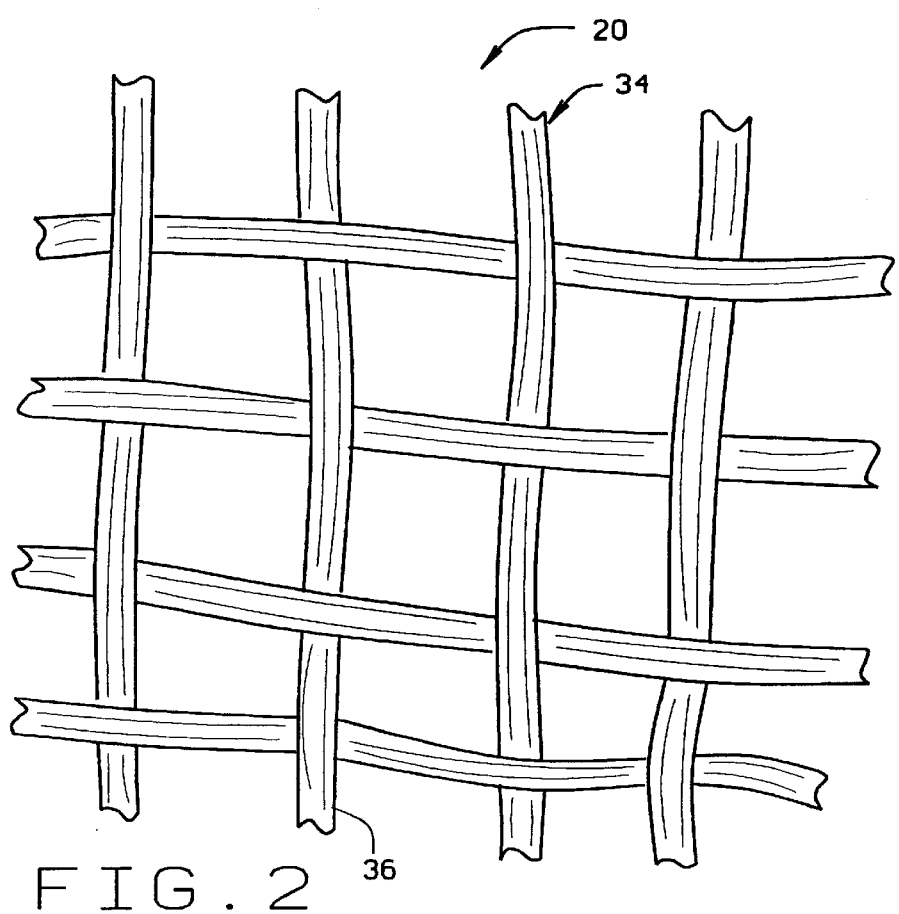
FIG. 2 is an enlargement of a weave formed from a plurality of complex fibers woven into a weave of memory material.

Referring now to FIG. 2, the memory material 20 as used in the bra embodiment of the parent invention, may be fashioned from a weave 34 comprised of a mesh or cross pattern of a plurality of individual complex fibers 36. Each complex fiber 36 may be a coil, spring, or serpentine arrangement of one or more strands of a shape memory alloy or, alternately, thin strips of shape memory alloy may be interweaved together and, by being able to glide past each other provide the necessary allowance for expansion and contraction of the material as it transitions between a first physical arrangement and a second physical arrangement. Although these constructions of the memory material are considered as preferable by the inventor in implementing his parent invention, as known to those of ordinary skill in the art still other constructions may be used in implementing the memory material, it only being required that its construction be amenable to allow for the desired excursion between the two physical arrangements as desired to effect a tensile force in an underlying soft tissue.

Figure 3:
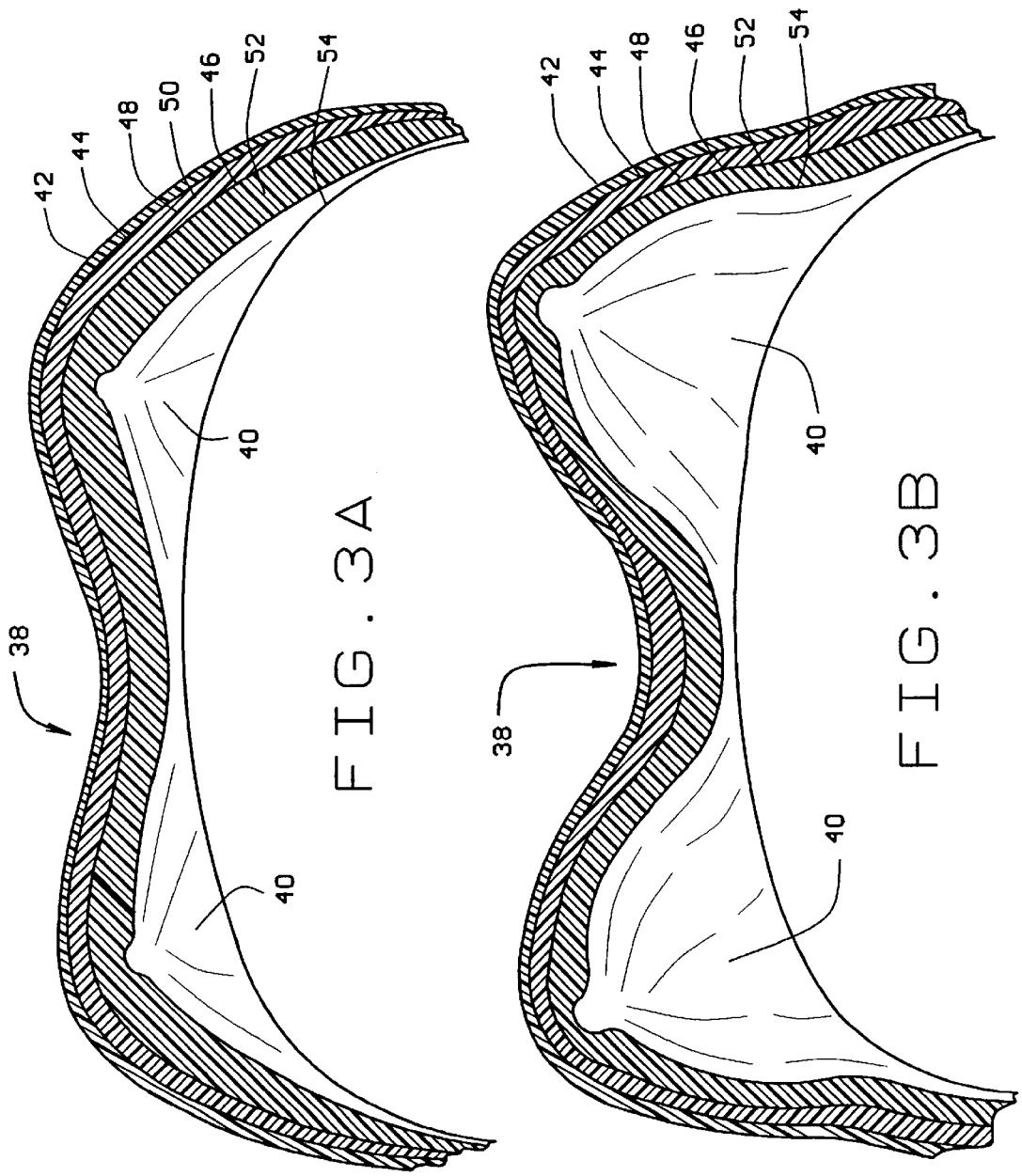
FIGS. 3*a*&*b* are cross sectional views of a bra incorporating the present invention with FIG. 3*a* depicting the bra configured as the memory material is in a first physical arrangement and FIG. 3*b* depicting the bra configuration as the memory material has transitioned into a second physical arrangement.
Figure 4:
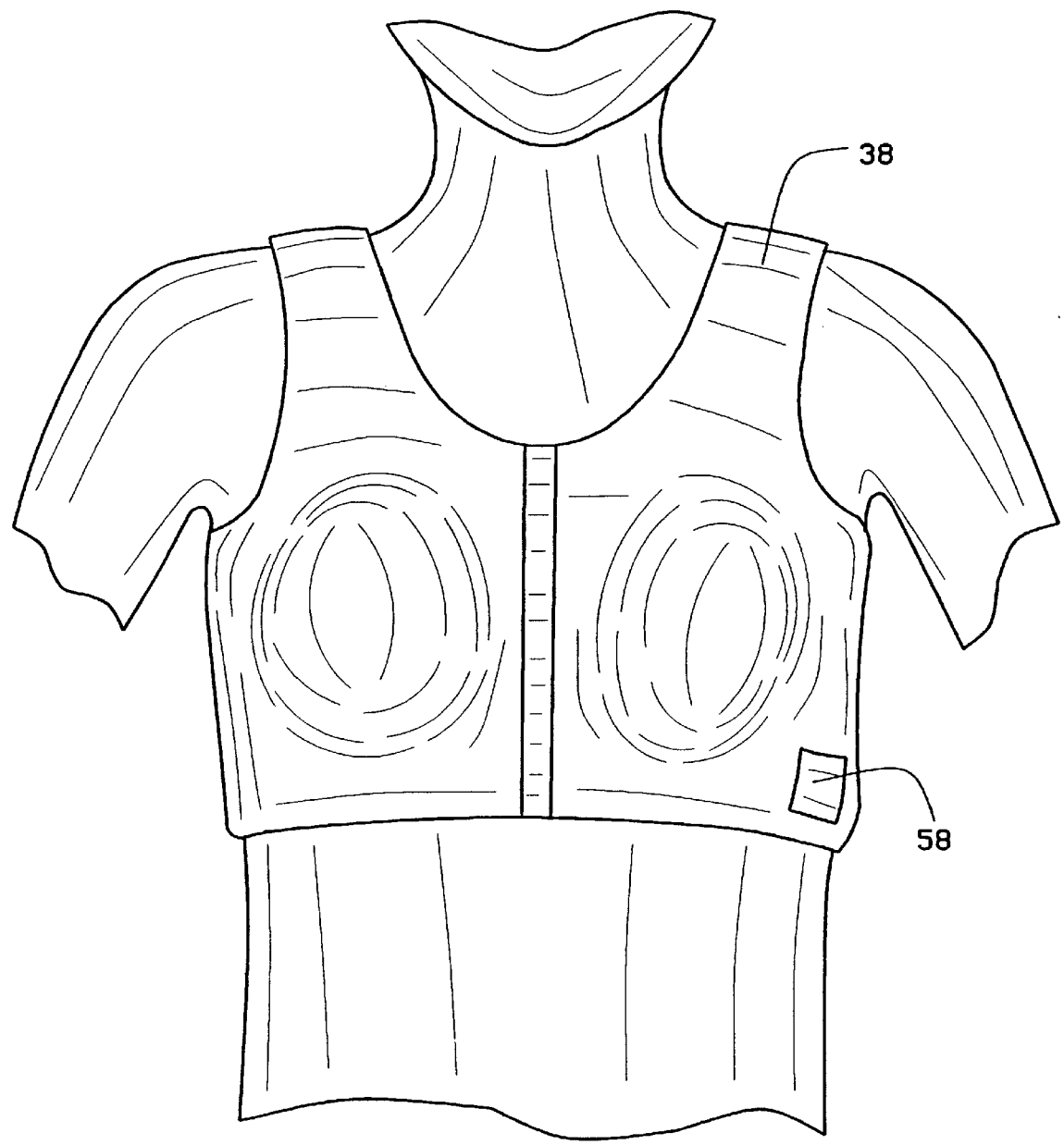
FIG. 4 depicts a frontal view of a patient wearing the bra embodiment of the invention.

As shown in FIGS. 3a and b, a bra 38 constructed in accordance with the teachings of the parent invention provides a good application for enlarging a patient's soft tissue such as a pair of female breasts 40. As shown therein, the bra 38 comprises a multi-layer construction. An outer layer 42 may be a supportive bra having an ornamental, aesthetic, or decorative covering as may be pleasing to the feminine eye. Beneath is preferably an outer layer of expandable or extensible material 44 which, with a corresponding similar layer 46, surrounds therebetween a layer 48 of memory material for imposing a tensile force as it is caused to move from the first physical arrangement as shown in FIG. 3a to the second physical arrangement as shown as FIG. 3b. The memory material 48 may be bathed by a lubricating fluid or gel 50 to facilitate the multiple cycling of the memory material between its two physical arrangements. A fluid layer, which may comprise a layer of gel 52 or an air or fluid filled bladder or other such spacer, may preferably then be provided to help conform the bra 38 to the body contour and to prevent pressure points and shear forces between the bra 38 and the underlying soft tissue 40. The fluid layer 52 may be confined itself inside an extensible envelope similar to the layers of extensible material 44, 46. Lastly, on the inside surface of the fluid layer 52, a layer of adhesive 54 may be applied to adhere the fluid layer 52 to the skin of the soft tissue 40 and to avoid any separation therebetween as the bra 38 is cycled between the positions shown in FIGS. 3a and b. Alternatively, a fluid may be provided instead of an adhesive layer with the adhesive forces thus being provided by surface tension. Indeed, the inventor contemplates that it may be preferable for a thin film of fluid to be provided as it is thought to be less susceptible to shear forces and therefore less likely to abrade the skin surface upon repeated use of the bra 38 over any extended period of time as might be recommended in a typical therapeutic regimen. As contemplated by the inventor, the bra 38 of the embodiment of the parent invention, as worn by a patient, is shown in FIG. 4.

Figure 5:
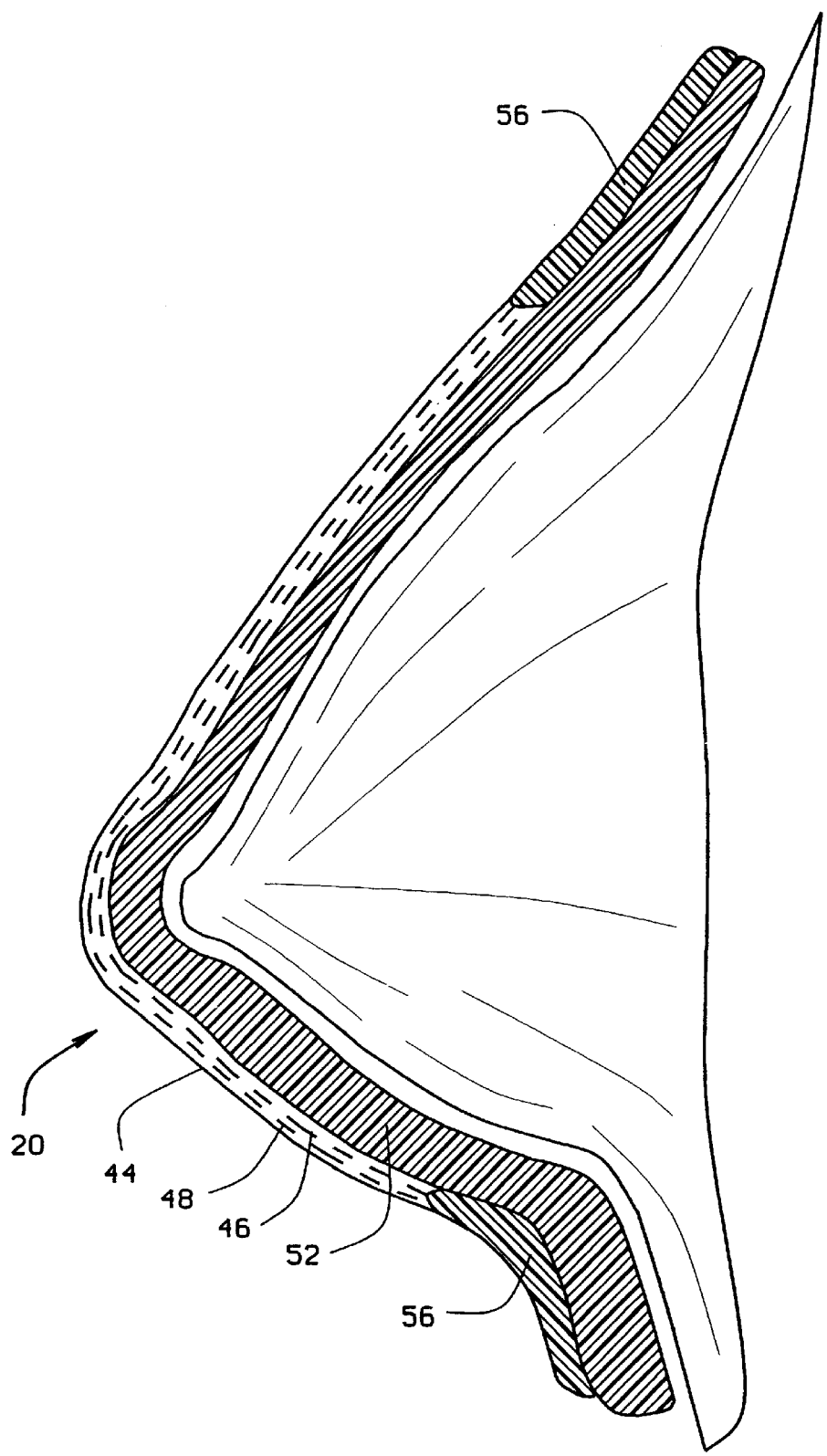
FIG. 5 is a cross sectional view detailing the bra embodiment of the invention as adhered to a breast.
Figure 6A:
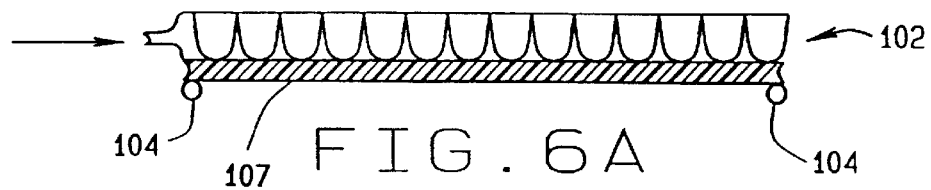
FIGS. 6*a*&*b* are cross-sectional views of a frame member shown in both a relaxed and an inflated state.
Figure 6B:
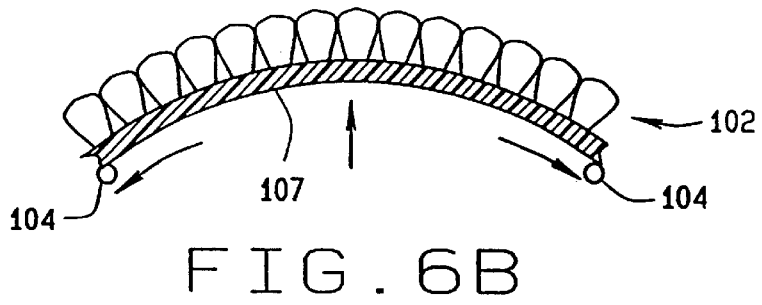

As is taught in several of his prior patents, the inventor contemplates that a ring, periphery, or lip 56, as best shown in FIG. 5, may be integrally formed as part of the dome 20, and surround it at its periphery, to support it against the patient's chest as the offsetting surface for the compressive force which balances the tensile force created by the bra 20. With this supporting ring 56, the domes 20 may be supported from the patient and thereby have their forces balanced to achieve an effective tensile force in the soft tissue as is required to achieve the purposes of the invention. For a more detailed explanation, reference is made to any one or more of the inventor's prior patents mentioned above. However, it should be noted that with the parent invention, the ring or periphery 56 may be either integrally formed with the dome 20 or constructed from material which does not exhibit the "memory" feature as is used to form the arcuate portion of the dome 20. Instead, any suitable structural material may be used with the memory material spanning the interior of the ring 56. With either embodiment, the inventor contemplates that a dome 20 could readily be constructed which would expand between two to three times its periphery which would correlate to a five times to ten times increase in surface area of the dome 20. With this degree of excursion, a substantial tensile force could be created although, as is known to those of ordinary skill in the art, lesser forces and smaller excursions could readily be provided for using the teachings herein as well as the known information relating to shape memory alloys and other types of memory materials.

For implementation as a breast enlargement device, such as with the bra embodiment of the invention as is explained in some detail herein, a bra could readily be constructed of a soft forming material at temperatures below body surface temperature, with the cup areas of the bra containing shape memory alloy fibers, weave, mesh, or sheets in its fabric. The bra would first have its memory material "set" in an appropriate shape, as predetermined to direct the growth in the chosen locations of the patient's breast by properly applying the desired tensile force. In other words, with the bra of the parent invention, the breast may be contoured and sculpted by encouraging growth in preselected areas to thereby fill in where needed. The bra is then placed on a patient, with appropriate attention being given to properly adhere the bra interior lining or gel to the skin of the breast by applying either a layer of fluid or adhesive. The bra cups are heated by the natural heat of the patient's breasts to approach the body surface temperature which is approximately thirty degrees centigrade. As the temperature of the bra rises, the shape memory alloy acts as a spring and as it returns to its "memory" configuration it exerts a tensile force on the patient's breasts, pulling the breasts along with them as they reconfigure into a deeper dome shape. With appropriate engineering design as would be known to those of ordinary skill in the art, the tensile force of the alloy spring weave/sheet can be appropriately adjusted to exert an evenly applied, or shaped uneven force to provide for sculpting of the breast, distending or distracting force substantially equal to the approximately 15 to 30 mmHg of pressure as taught with the inventor's prior vacuum type bra devices. Alternately, a greater or lesser tensile force could be engineered as desired depending upon the appropriate therapeutic regimen recommended, or as learned to be more physiologically effective through greater clinical experience with the bra of the parent invention. Additionally, several of the fibers may be set at a higher transition temperature and then activated by a battery powered electronic circuit 58 to cycle intermittently to thereby provide a supplemental tensile force, as desired. The battery powered electronic circuit 58 may be appropriately concealed at any convenient point on the bra, and connected to those fibers selected to be in the region of interest to apply the force in the manner and location desired. Further refinement of the construction and design using finite element analysis, as would be well known to those of ordinary skill in the art, can maintain this tensile force constant as the spring like reversion pulls from a flat sheet to a spherical structure having a depth even greater than a hemisphere.

While the embodiment best explained herein relates to the use of a bra to expand the female breast, it would be apparent to those of ordinary skill in the art that the parent invention may also be used in other applications without undue experimentation. Examples of these include as a simple soft tissue expander as might be useful for replacing collagen and fat injections and other aloplastic implants typically used in the prior art to improve contour defects caused by aging, involution or scarring. With an appropriately designed mask to be worn at night, for example, wrinkles, dimples, lips and even sunken or hollowed features of the face may be filled by expanded soft tissue whose growth would be induced by the present invention. For such applications, the dome and surrounding lip or periphery would be used.

It should also be apparent to those of ordinary skill in the art that the particular fluid utilized to create the surface tension for achieving adherence between the fluid layer or other liner surface may be chosen from amongst many suitable fluids including mineral oil, baby oil, water, physiologic saline, various kinds of water or oil based gels, glycerine, creams, and ointments, all of which have been found to adhere to the skin surface and withstand tensile forces in excess of the approximate 15 to 30 mmHg required in various therapeutic regimens with the vacuum based device. In several of those embodiments, a thin membrane is bonded to the skin and the vacuum is generated in the enclosed space between the inner surface of the membrane and the dome. In this embodiment, surface tension has been successfully implemented by the inventor. Furthermore, it is believed that the thin membrane embodiment may also be successfully implemented in the memory material embodiment as disclosed and claimed herein.

Figure 7A:
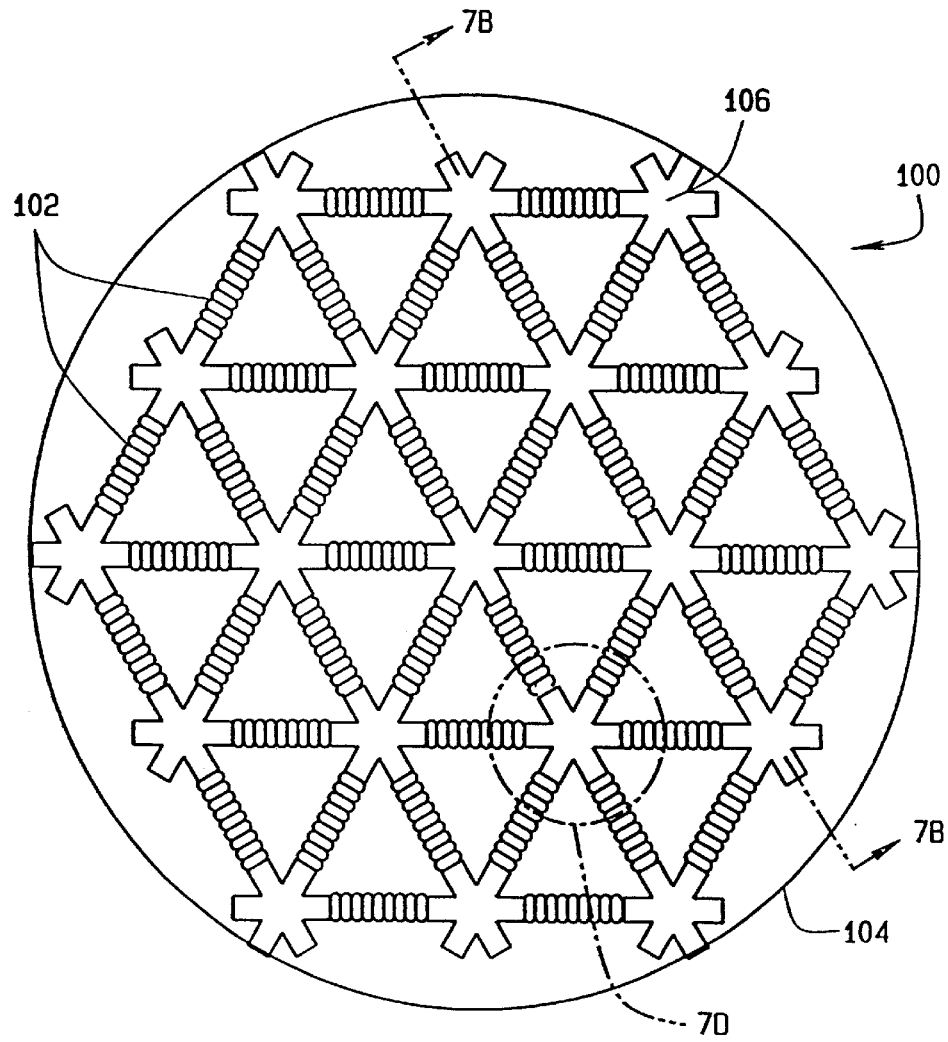

The inventor has further advanced his invention to include the construction of an expanding frame 100 for soft tissue distraction. In one embodiment of the present invention as shown in FIGS. 6a–b and 7a–d, the frame 100 is arranged in the pattern of a geodesic dome 101. The frame 100 is comprised of a plurality of arranged struts or legs 102 which may be individually inflated to cause them to lengthen, and to constrain that lengthening by a peripheral restraint 104 in order to force a two dimensional lengthening. This is shown in FIG. 7a as a matrix of triangles formed in an overall shape of a hexagon. However, any other polygonal shape of convenience could be used as well, so long as the desired distractive force may be induced in the underlying tissue. With the use of struts that exhibit the necessary resiliency to achieve the desired excursion, nodes or junctures 106 may be used that are rigid to provide an overall strength to the frame. Also, support rods 107 may be provided conveniently within the central core of one or more struts 102 and serve to limit their excursion and help distribute the loading so as to achieve the desired distribution of distractive forces across the underlying soft tissue. FIGS. 7b–d show further detail of the frame 100, struts 102, and nodes 106.

The basic polygon need not be a triangle like in the classical geodesic dome but could be an assemblage of squares, pentagons, rings, circles, or other shapes. There are a number of alternate related options to this geodesic structure version. The frame 100 may be constructed in the pattern of a Florentine dome 108, (FIG. 8) for example, comprising radially and circumferentially connected linearly expanding struts 109. In this scenario, the original grid is that of concentric circles 110 interconnected by a number of radial rays 112 originating from the center 114. Again, as in the geodesic version, the peripheral edges 116 at the rim of the expanding frame 100 should be prevented from stretching. To accommodate the increased surface, the frame 100 is forced to rise into the dome 108 upon inflation.

Figure 9:
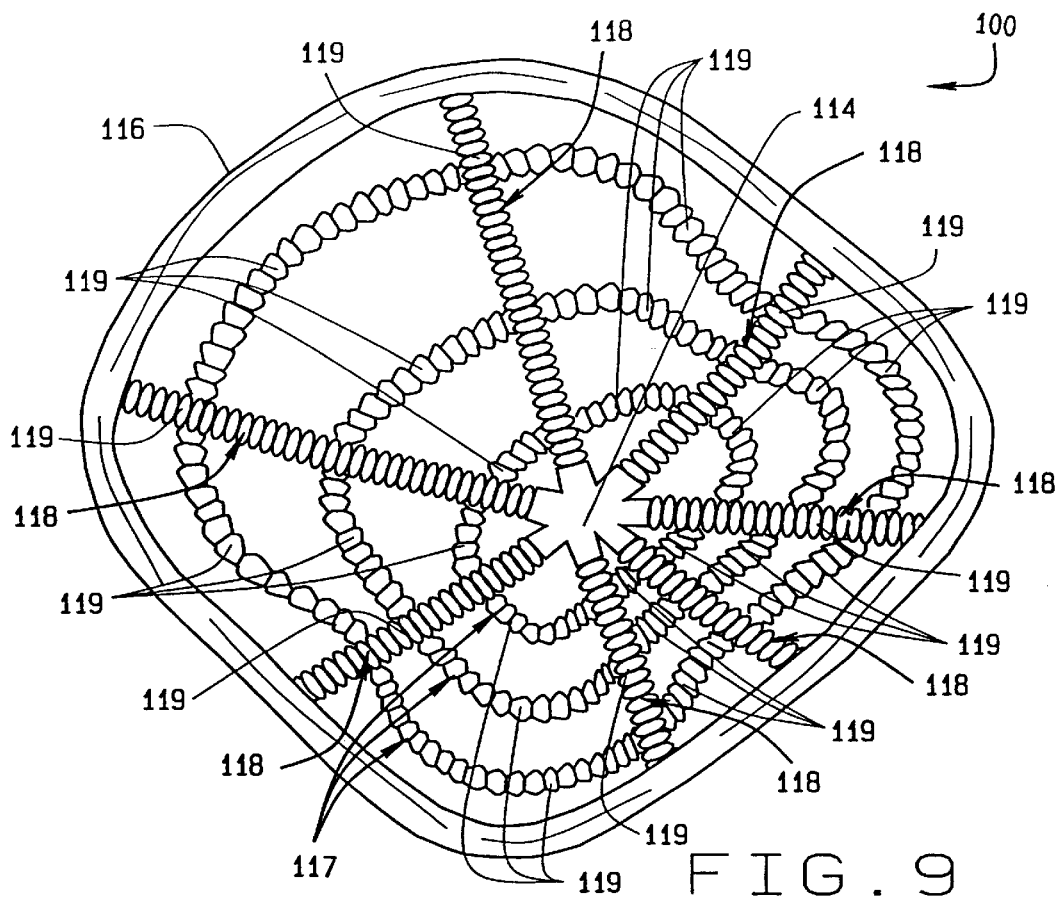
FIG. 9 depicts a frame constructed to apply a differential force to various underlying tissue areas, as would be desired for use with a complex surface area.
Figure 12A:
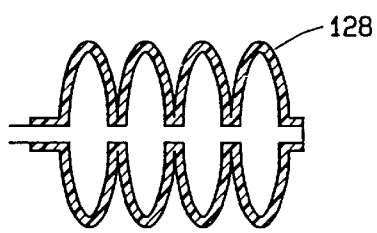
FIGS. 12a&b are cross-sectional views of a cellular construction, in both a relaxed and inflated configuration, for a frame member.
Figure 12B:
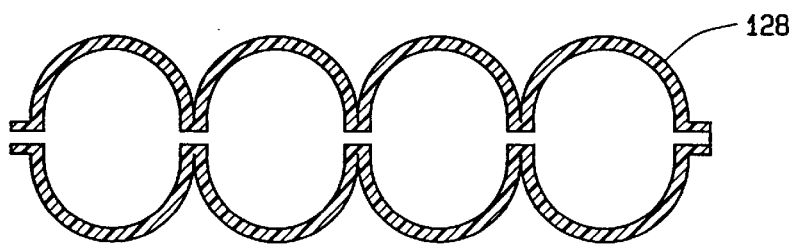

In yet a more general form of this version, the pattern of the frame 100 need not be concentric circles but can be a series of complex closed curves 117 similar to the altitude lines in the map of a mountain, as shown in FIG. 9. These expanding curves 117 are preferably held together by a series of interconnecting radially expanding rays 118. Pressure inside such a construct will cause it to stretch and depending upon the peripheral edge constraint 116, to rise like a dome with a shape dictated by the geometrical arrangement of the curves 117 and the linear rays 118.

Figure 10:
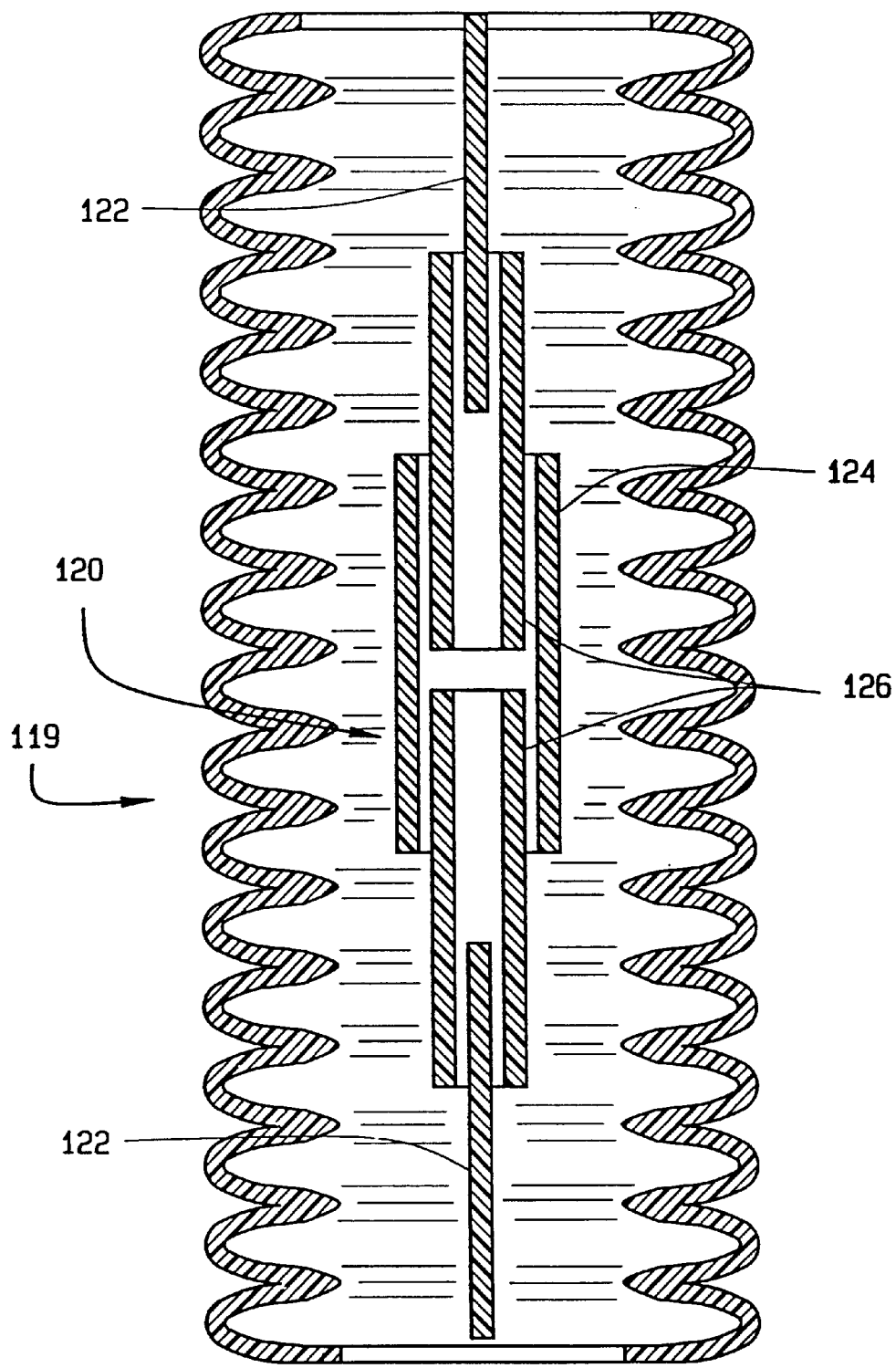
FIG. 10 depicts a cross-sectional view of a segment or strut which could be used to form any one or more of the frames.

To prevent serpentine-like elongation instead of the desired rigid linear expansion of the individual segments or struts 119, an internal reinforcement in the form of semi-rigid telescopic mechanical backbone 120 may be included as needed, as shown in FIG. 10. This mechanical backbone 120 is preferably formed from a pair of opposed rods 122, with a sliding joinder 124 overlying their inner ends 126 and providing a limited and defined (and otherwise controlled) excursion within each strut 119. Indeed, different backbones 120 may be provided in different struts 119 within the same frame 100 so as to more exactly design and tailor the desired excursion at different locations within the frame 100. This would be especially desirable to match complex surface contours intended to be "grown".

Figure 11:
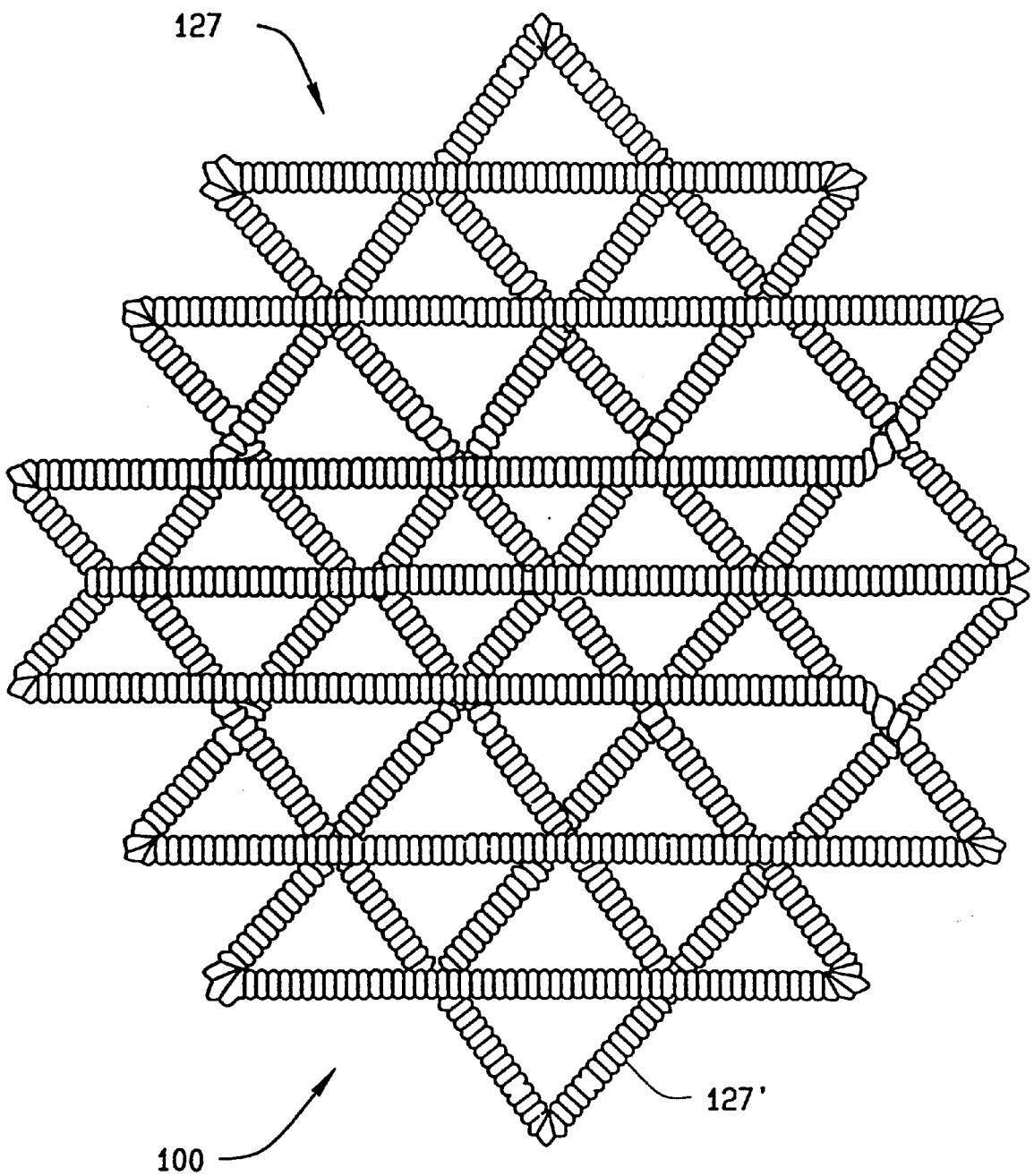
FIG. 11 is a front view of a frame formed of triangular members.
Figure 13A:
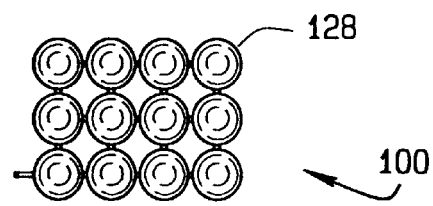
FIGS. 13a&b are top views of the cellular construction frame member of FIG. 12.
Figure 13B:
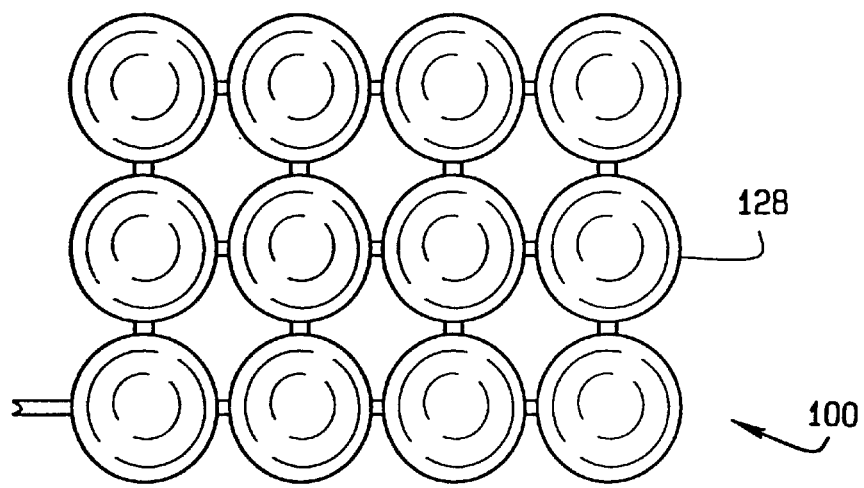

This corrugated/expanding cylinder version does not need to consist of individual well-defined segments or struts separated by connectors. The entire frame construct 100 can be judiciously molded into a semi-continuous sheet 127 of corrugations 127' running and expanding in various directions. For example, FIG. 11 shows a continuous pattern of triangles. However, these could also rings, disks or any closed polygon. The extent of expansion with inflation is determined by the physical/mechanical characteristics of the material used and by the depth of the in-foldings of the corrugations 127'; with deeper corrugations 127' allowing more excursion with inflation. Of course, this construction provides even greater design opportunity for creating the frame 100 to match any desired surface.

A yet more generalized version of the frame 100 with corrugated design 127 would comprise a sheet-like array of inflatable fusiform 128 or elongated football shaped cells interconnected at the waist, as shown in FIGS. 12a–b and 13a–b. Positive pressure inside these elongated fusiform cells 128 will cause them to widen and assume a spherical shape. In doing so, they push each other out in all directions causing the desired two-dimensional spread of the frame 100 (see FIGS. 12a–b and 13a–b). This may be conveniently referred to as the egg crate version.

Figure 14A:
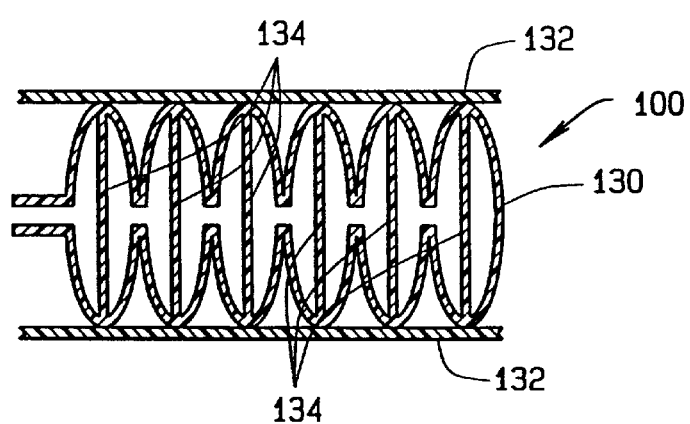
FIGS. 14a&b are cross-sectional views of an inflatable cell construction having a network of non-expandable interconnecting links sandwiched between two expandable membranes in both a relaxed and inflated view.

An alternative means of achieving this restricted two-dimensional expansion is to form the frame 100 with an array of inflatable cells 130 sandwiched between two expandable membranes 132 that are prevented from separating through a network of non-expandable interconnecting links 134 as depicted in FIGS. 14a–b. It is noted that this is similar to the design initially depicted above in FIG. 6. With inflation, the individual cells, originally fusiform 128 (as in the egg crate version) cannot get taller because of the restraining ligament or interconnecting link 134 in their central core; they can only get fat. With increasing pressure of inflation progressively fatter cells push each other out to induce a widening and a two-dimensional spread of the frame 100, instead of a simple inflation or ballooning out of the sandwich. This is conveniently referred to as the enrobed restrained version of the egg crate. Instead of fusiform or cellular construction, the frame 100 could be comprised also of a continuous membrane which could be wrinkled or otherwise mechanically collapsed and which would then unfold upon inflation. With this construction, a pair of sheet-like members could be joined at various locations across the surface of the sheets and multiple members joined to form the frame 100. Still another embodiment of the frame 100 is comprised of a plurality of polygon-shaped members which are individually inflatable and which are themselves joined together to form the entirety of the frame. For example, each individual polygon could be formed in the shape of a triangle and multiple triangles could be joined at their corners to form the frame, or circles or other curvilinear, regular or irregularly shaped individual cells could be interconnected into an array.

In all of the newest embodiments, an internal backbone mechanical framework of telescopic studs might be added to control the movement and rigidity to the construct or strut 119, as shown in FIG. 10.

Referring to FIGS. 15a–b, another detail of the newest embodiment of the present invention may be commented on. This is the mechanical coupling of the expandable frame 100 to expandable membranes 142a,142b, where the membrane 142b in turn is in contact with the tissues to be expanded. By virtue of its design, the expanding frame 100 pushes outward while pulling behind it a smooth concave surface 144 for even contact with the tissues. The moving segments of the frame 100 are not necessarily smooth (they will have inherent dimples and ridges) and there could be some difficulty in gluing them to a concave smooth surface, i.e. the underlying soft tissue. To overcome this, the expanding frame 100 may be conveniently sandwiched between two expandable membranes 142a,142b and a space 146 between these two membranes 142a,142b sealed and filled with a fluid 148. Induced negative pressure in the fluid 148 caused by the elevation of the frame 100 and pull of the outer membrane 142a will provide the mechanical link between them, and force the inner membrane 142b at the concave surface 144 to rise in unison.

Depending upon its mechanical characteristics, the stretching or distracting force can be adjusted to provide a constant distraction force equal in magnitude to the force generated by the vacuum used in the inventions previously disclosed in the inventor's prior patents. This force of distraction can be engineered to remain constant over the normal range of excursion, or to be altered, through use of the various mechanisms mentioned herein. In the case of the use of the present invention to expand the breast, an excursion may preferably range from the relatively small breast shape to a large D cup size. (From flat to ~⅝ sphere).

The technology used to "grow" the breast can similarly be applied to expand any body part and in particular can be used to fill up the face. These devices, including the newest embodiments would be applied over the wrinkle lines and/or the entire face. Under the effect of sustained distraction and over a period of time, the atrophic subcutaneous tissues of the aged face can be filled up with newly generated stretch induced tissue. The rejuvenating face mask and the wrinkle patch preferably uses the same kind of expandable rubber membrane and expansion frame used in the breast device. Surface tension supplied by a hydrating gel (a widely used cosmetic product) preferably provides the mechanical link between the device and the facial skin.

Various changes and modifications to the invention would be apparent to those of ordinary skill in the art. Those changes, variations, and modifications are fairly included in the scope of the present invention which should be considered as limited by only by the scope of the claims appended hereto and their legal equivalents.

What is claimed is:

1. A device for expanding a patient's soft tissue, said device comprising a frame adapted for attachment to a soft tissue site desired to be expanded, said frame comprising at least one frame member which is inflatable to expand the frame and induce a distractive force in the underlying soft tissue site.

2. The device of claim 1 wherein said frame is comprised of a plurality of inflatable frame members, and further comprising a peripheral restraint surrounding said frame to restrict lateral movement of said frame as the frame members are inflated.

3. The device of claim 2 wherein said frame members are arranged in a plurality of polygons.

4. The device of claim 2 further comprising a stabilizer rod contained within at least one of said frame members and positioned to control the movement of said frame member as said frame member is inflated.

5. The device of claim 2 wherein said frame members are arranged in an asymmetric shape.

6. The device of claim 2 wherein said frame members are formed from a bellows material to allow for their expansion and contraction in response to their inflation and deflation, respectively.

7. The device of claim 1 wherein said frame is comprised of a plurality of interconnected generally spherically shaped cells.

8. The device of claim 7 further comprising at least one membrane attached to said frame and extending over a substantial portion thereof.

9. The device of claim 8 further comprising a second membrane, said frame being sandwiched between said membranes, and one of said membranes being adapted to be adhered to the underlying soft tissue.

10. The device of claim 9 further comprising at least one reinforcing rod contained within said frame.

11. The device of claim 10 further comprising a plurality of reinforcing rods contained within said frame, one of said rods being contained within substantially each of the cells comprising the frame.

12. The device of claim 1 further comprising at least one membrane attached to said frame and extending over a substantial portion thereof.

13. The device of claim 12 further comprising a second membrane, said frame being sandwiched between said membranes, and one of said membranes being adapted to be adhered to the underlying soft tissue.

14. The device of claim 13 further comprising a fluid substantially filling said space between said membranes.

15. A device for expanding soft tissue, said device comprising an inflatable frame contained within two flat, sheet-like membranes, one of said membranes being adapted for attachment across a substantial portion of its width and length to the underlying tissue.

16. The device of claim 15 further comprising a peripheral restrictor surrounding said frame.

17. The device of claim 16 wherein said frame is comprised of a plurality of frame members, at least one of which is inflatable.

18. The device of claim 17 wherein said frame members are arranged in a plurality of polygons.

19. The device of claim 16 wherein said frame is comprised of a plurality of cells, said cells being interconnected and inflatable.

20. The device of claim 19 further comprising a plurality of mechanical supports contained within said frame cells to restrict their movement as the frame is inflated.

21. A bra for enlarging a patient's breast size, said bra comprising at least one dome for adhering to a patient's breast, said dome including a supporting frame, said frame having at least one frame member which is inflatable to expand the frame and induce a distractive force in the underlying breast.

22. The bra of claim 21 wherein said frame is comprised of a plurality of inflatable frame members.

23. The bra of claim 22 further comprising a peripheral restraint surrounding said frame to restrict lateral movement of said frame as the frame members are inflated.

24. The bra of claim 21 wherein said inflatable frame member is comprised of fusiform.

25. The bra of claim 22 wherein said plurality of inflatable frame members comprise an array of fusiform.

26. The bra of claim 22 further comprising an outer membrane covering the frame and an inner membrane covering the frame, the inner membrane being adapted for being adhered to the breast.

27. The bra of claim 26 further comprising a fluid substantially filling the space between the membranes.

28. The bra of claim 22 wherein said frame members are arranged in a geometric pattern.

29. The bra of claim 22 wherein said frame members are arranged in an asymmetric pattern.

30. The bra of claim 22 further comprising a mechanical support for said frame to restrict the movement of said frame as the frame members are inflated.

31. The bra of claim 22 further comprising a mechanical limiter associated with at least one of said frame members to limit the movement thereof and thereby define a shape of the inflated frame and the dome as desired.

32. A bra for enlarging a patient's breast size, said bra comprising a pair of domes for adhering to a patient's breast, each of said domes including a supporting frame, said frame being comprised of a plurality of inflatable frame members so that as said frame members are inflated, the frame is expanded to induce a distractive force in the patient's underlying breasts.

33. The bra of claim 32 wherein said frame is contained between a pair of membranes, one of said membranes being adapted to adhere to the patient's breasts.

34. The bra of claim 33 further comprising a mechanical limiter associated with each of the frames to limit the excursion of said frames as they are inflated to thereby apply the distractive force as desired.

35. The bra of claim 34 wherein said frames are arranged in egg crate fashion.

36. The bra of claim 34 wherein said frames are formed of fusiform.

* * * * *